(12) United States Patent  
Mihan

(10) Patent No.: US 7,202,373 B2
(45) Date of Patent: Apr. 10, 2007

(54) MONOCYCLOPENTADIENYL COMPLEXES

(75) Inventor: Shahram Mihan, Bad Soden (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/525,215

(22) PCT Filed: Aug. 18, 2003

(86) PCT No.: PCT/EP03/09125

§ 371 (c)(1),
(2), (4) Date: Feb. 22, 2005

(87) PCT Pub. No.: WO2004/018489

PCT Pub. Date: Mar. 4, 2004

(65) Prior Publication Data

US 2006/0004215 A1 Jan. 5, 2006

(30) Foreign Application Priority Data

Aug. 22, 2002 (DE) ................. 102 39 275

(51) Int. Cl.
C07F 17/00 (2006.01)
B01J 31/00 (2006.01)
C08F 4/44 (2006.01)
(52) U.S. Cl. ............... 556/7; 546/2; 526/161; 526/178; 526/198; 526/348; 502/103; 502/117
(58) Field of Classification Search ........... 556/7; 502/103, 117; 526/161, 178, 198, 348; 546/2
See application file for complete search history.

(56) References Cited

U.S. PATENT DOCUMENTS

| 3,242,150 | A | 3/1966 | Scoggin ............ 260/88.2 |
| 3,248,179 | A | 4/1966 | Norwood ............ 23/285 |
| 3,709,853 | A | 1/1973 | Karapinka ......... 260/88.2 D |
| 4,015,059 | A | 3/1977 | Karol ............... 526/130 |
| 5,547,675 | A | 8/1996 | Canich ............. 502/117 |
| 5,808,122 | A | 9/1998 | Herrmann et al. ...... 556/58 |
| 6,160,145 | A | 12/2000 | Wu et al. ............ 556/27 |
| 6,255,418 | B1 | 7/2001 | Jolly et al. .......... 526/160 |
| 6,284,905 | B1* | 9/2001 | Ashe et al. ........... 556/7 |
| 6,417,302 | B1 | 7/2002 | Bohnen ............. 526/160 |
| 6,437,161 | B1 | 8/2002 | Mihan et al. ......... 556/11 |
| 6,589,905 | B1 | 7/2003 | Fischer et al. ....... 502/300 |
| 6,699,948 | B2 | 3/2004 | Mihan et al. ........ 526/161 |
| 6,756,505 | B1 | 6/2004 | Kristen et al. ........ 556/7 |
| 6,784,261 | B1 | 8/2004 | Schopf et al. ........ 526/16 |
| 6,812,185 | B2 | 11/2004 | Fischer et al. ....... 502/120 |
| 6,911,516 | B1 | 6/2005 | Mihan et al. ........ 526/348 |
| 7,045,644 | B2 | 5/2006 | Schopf et al. ........ 556/63 |
| 7,053,160 | B1 | 5/2006 | Bingel et al. ........ 526/170 |
| 2003/0236164 | A1 | 12/2003 | Fischer et al. ....... 502/439 |
| 2004/0214970 | A1 | 10/2004 | Schopf et al. ....... 526/159 |

FOREIGN PATENT DOCUMENTS

| DE | 19630580 | 2/1998 |
| DE | 19710615 | 9/1998 |
| EP | 0742046 | 11/1996 |
| WO | 9109882 | 7/1991 |
| WO | 9600243 | 1/1996 |
| WO | 9613529 | 5/1996 |
| WO | 9704015 | 2/1997 |
| WO | 9736937 | 10/1997 |
| WO | 9822486 | 5/1998 |
| WO | 9827124 | 6/1998 |
| WO | 9840419 | 9/1998 |
| WO | 9906414 | 2/1999 |
| WO | 0005277 | 2/2000 |
| WO | 0020426 | 4/2000 |
| WO | 0024787 | 5/2000 |
| WO | 0031090 | 6/2000 |
| WO | 0035928 | 6/2000 |
| WO | 0109148 | 2/2001 |
| WO | 0112687 | 2/2001 |
| WO | 0141920 | 6/2001 |
| WO | 0192346 | 12/2001 |

OTHER PUBLICATIONS

K. H. Theopold et al., "Constrained Geometry Chromium Catalysts for Olefin Polymerization," *Organometallics*, vol. 15(25), p. 5284-5286 (1996).

P. Jutzi et al, "Cyclopentadienyl compounds with nitrogen donors in the side-chain," *Journal of Organometallic Chemistry* 500, p. 175-185 (1995).

M. Enders et al., "8-Quinolylcyclopentadienyl, a Ligand with a Tailored Fit for Chelate Complexes," *Chem. Ber.*, vol. 129, p. 459-463 (1996).

M. S. Blais et al., Pendent Aminoalkyl-Substituted Monocyclopentadienyltitanium Compounds and Their Polymerization Behavior, *Organometallics*, vol. 17(17), p. 3775-3783 (1998).

T. Mise et al., "Preparation and structure of the *ansa*-molybdenocene and tungstenocene derivatives. Reaction of [O(SiMe$_2$C$_5$H$_4$)$_2$]MoH$_2$ with methyl methacrylate to probe the olefin attacking site," *Journal of Organometallic Chemistry*, vol. 473, p. 155-162 (1994).

(Continued)

Primary Examiner—Porfirio Nazario-Gonzalez
(74) Attorney, Agent, or Firm—Jarrod N Raphael

(57) ABSTRACT

Monocyclopentadienyl complexes in which the cyclopentadienyl system bears at least one uncharged donor bound via a boron-containing bridge and comprising one or more atoms of group 15 and/or 16 of the Periodic Table of the Elements and is bound to a metal selected from the group consisting of titanium in the oxidation state 3, vanadium, chromium, molybdenum and tungsten, a catalyst system comprising at least one of the monocyclopentadienyl complexes, the use of the catalyst system for the polymerization or copolymerization of olefins and a process for preparing polyolefins by polymerization or copolymerization of olefins in the presence of the catalyst system and polymers obtainable in this way.

12 Claims, No Drawings

OTHER PUBLICATIONS

A. Döhring et al., "Donor-Ligand-Substituted Cyclopentadienylchromium (III) Complexes: A New Class of Alkene Polymerization Catalyst. 1. Amino-Substituted Systems," *Organometallics*, vol. 19(4), p. 388-402 (2000).

B. Kirk-Othmer, "Olefin Polymers (High Pressure Polyethylene); High Pressure (Low and Intermediate Density) Polyethylene," *Encyclopedia of Chemical Technology*, vol. 16, p. 402-420 (1981).

R. Halterman, "Synthesis and Applications of Chiral Cyclopentadienylmetal Complexes," *Chem. Rev.*, vol. 92(5), p. 965-994 (1992).

S. Strauss, "The Search for Larger and More Weakly Coordinating Anions," *Chem. Rev.*, vol. 93(3), p. 927-942 (1993).

L. Resconi et al., "Selectivity in Propene Polymerization with Metallocene Catalysts," *Chem. Rev.*, vol. 100(4), p. 1253-1345 (2000).

L. Fieser & M. Fieser, "III. Die Steroide," *Lehrbuch Der Organischen Chemie*, Verlag Chemie, 3rd revised edition, Weinheim, p. 366-376 (1958)—includes Table of Contents.

H. Brintzinger et al., "*ansa*-Metallocene derivatives—XVII. Racemic and *meso* diastereomers of group IV metallocene derivatives with symmetrically substituted, dimethylsilanediyl-bridged ligand frameworks. Crystal structure of R, S-Me$_2$Si(3-t-Bu-5-MeC$_5$H$_2$)$_2$ZrCl$_2$," *Journal of Organometallic Chemistry*, vol. 369, p. 359-370 (1989).

M. Brookhart et al., "Highly Active Iron and Cobalt Catalysts for the Polymerization of Ethylene," *J. Am. Chem. Soc.*, vol. 120(16), p. 4049-4050 (1998).

V. Gibson et al., "Novel olefin polymerization catalysts based on iron and cobalt," *Chem. Commun.*, p. 849-851 (1998).

G. Herberich et al., "Borylcyclopentadienides," *Organometallics*, vol. 15(1), p. 58-67 (1996).

M. Enders et al., "Chirale Titan- und Zirkoniumkomplexe mit dem 1-(8-Chinoyl)-2,3-dimethylcyclopentadienyl-Liganden," *Journal of Organometallic Chemistry 549*, p. 251-256 (1997).

Araki et al., Abstract 160483p—"Syntheses and structures of transition-metal complexes of mesoionic olate, thiolate, selenolate, and cyclopentadienide," *Chemical Abstracts*, vol. 119(15), p. 957 (1993).

J Ewen et al., "Expanding the Scope of Metallocene Catalysis: Beyond Indenyl and Fluorenyl Derivatives," Metalorganic catalysts for synthesis and polymerization, *Springer Verlag*, p. 150-169 (1999).

H. Braunschweig et al., "The chemistry of [1]borametallocenophanes and related compounds," *Journal of Organometallic Chemistry*, vol. 680(1-2), p. 31-42 (2003) XP004450650.

H. Braunschweig et al., "Synthesis and Structure of the First [1]Boratitanocenophanes," *Eur. J. Inorg. Chem.*, p. 69-73 (1999).

J. Hartwig et al., "Structural and Reaction Chemistry of Tungstenocene Boryl Complexes," *Organometallics*, vol. 15(25), p. 5350-5358 (1996).

R. Duchateau e al., "Synthesis of Cyclopentadienyl-, Indenyl-, and Fluorenylbis (pentafluorophenyl)boranes as Ligands in Titanium and Zirconium Half-Sandwich Complexes. The Crystal Structures of C$_{13}$H$_9$B(C$_6$F$_5$)$_2$·*t*-BuNH$_2$, C$_{13}$H$_8$SiMe$_3$B(C$_6$F$_5$)$_2$, and {η$^5$-C$_5$H$_4$B(C$_6$F$_5$)$_2$}TiCl$_3$," *Organometallics*, vol. 16(23), p. 4995-5005 (1997).

G. Zi et al., "Synthesis, Structural Characterization, and Catalytic Property of Group 4 Metal Carborane Compounds with a *i*Pr$_2$-NB-Bridged Constrained-Geometry Ligand," *Organometallics*, vol. 21(19), p. 3850-3855 (2002).

M. Enders et al., "Activation of σ- and π-Bonds by Metal Complexes with Hemilabile Quinolyl Cyclopentadienyl Ligands," Part I, Abstract D091, *18th Conference on Organometallic Chemistry*, Munich, Aug. 16-21, 1998.

* cited by examiner

MONOCYCLOPENTADIENYL COMPLEXES

The present invention relates to monocyclopentadienyl complexes in which the cyclopentadienyl system bears at least one uncharged donor bound via a boron-containing bridge and to a catalyst system comprising at least one of the monocyclopentadienyl complexes.

In addition, the invention relates to the use of the catalyst system for the polymerization or copolymerization of olefins and to a process for preparing polyolefins by polymerization or copolymerization of olefins in the presence of the catalyst system and to polymers obtainable in this way.

Many of the catalysts which are used for the polymerization of α-olefins are based on demobilized chromium oxides (cf., for example, B. Kirk-Othmer, "Encyclopedia of Chemical Technology", 1981, vol. 16, p. 402). These give, inter alia, ethylene homopolymers and copolymers having high molecular weights, but are relatively insensitive toward hydrogen and thus do not allow the molecular weight to be controlled in a simple fashion. In contrast, the use of bis(cyclopentadienyl)-chromium (U.S. Pat. No. 3,709,853), bis(indenyl)chromium or bis(fluorenyl)chromium (U.S. Pat. No. 4,015,059) which has been applied to an inorganic, oxidic support allows the molecular weight of polyethylene to be controlled in a simple manner by addition of hydrogen.

As in the case of Ziegler-Natta systems, there is also now a desire for catalyst systems based on these chromium compounds having a uniquely defined, active center, namely single-site catalysts. Activity, copolymerization behavior of the catalyst and the properties of the polymers obtained in this way should be able to be altered in a simple fashion by targeted variation of the ligand framework.

Thus, EP 0742 046 claims constrained geometry complexes of transition group 6, a specific process for preparing them (via metal tetraamides) and a process for preparing a polyolefin in the presence of such catalysts. Polymerization examples are not given. The ligand framework comprises an anionic donor which is linked to a cyclopentadienyl radical.

In Organomet. 1996, 15, 5284–5286, K. H. Theopold et al. describe an analogous {[(tert-butyl-amido)dimethylsilyl](tetramethylcyclopentadienyl)}chromium chloride complex for the polymerization of olefins. This complex selectively polymerizes ethylene. Comonomers such as hexene are not incorporated, nor can propene be polymerized.

This disadvantage can be overcome by use of structurally very similar systems. Thus, DE 197 10615 describes monocyclopentadienylchromium compounds substituted by donor ligands by means of which, for example, propene can also be polymerized. In these compounds, the donor is from group 15 and is uncharged. The donor is bound to the cyclopentadienyl ring via a $(ZR_2)_n$ fragment, where R is hydrogen, alkyl or aryl, Z is an atom of group 14 and $n \geq 1$. DE 196 30 580 specifically claims Z=carbon in combination with an amine donor.

WO 96/13529 describes reduced transition metal complexes of groups 4 to 6 of the Periodic Table having polydentate monoanionic ligands. These include cyclopentadienyl ligands bearing a donor function. The examples are restricted to titanium compounds.

There are also ligand systems in which the donor group is joined rigidly to the cyclopentadienyl radical. Such ligand systems and their metal complexes are summarized, for example, by P. Jutzi and U. Siemeling in J. Orgmet. Chem. (1995), 500, 175–185, section 3. In Chem. Bar. (1996), 129, 459–463, M. Enders et. al. describe 8-quinolyl-substituted cyclopentadienyl ligands and their titanium and zirconium trichloride complexes. 2-Picolylcyclopentadienyltitanium trichloride in combination with MAO has been used by M. Blais, J. Chien and M. Rausch in Organomet. (1998), 17 (17) 3775–3783, for the polymerization of olefins.

WO 00/35928 discloses, inter alia, metallocene complexes having a donor bound via a boron-containing bridge and containing a central metal from group 4, 5 or 6. Examples containing uncharged donors are not described.

It is an object of the present invention to find further transition metal complexes based on cyclopentadienyl ligands having a bridged donor which are suitable for the polymerization of olefins.

We have found that this object is achieved by monocyclopentadienyl complexes in which the cyclopentadienyl system bears at least one uncharged donor bound via a boron-containing bridge and comprising one or more atoms of group 15 and/or 16 of the Periodic Table of the Elements and is bound to a metal selected from the group consisting of titanium in the oxidation state 3, vanadium, chromium, molybdenum and tungsten.

Possible donors are uncharged functional groups containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide or unsubstituted, substituted or fused, heterocyclic ring systems. In this context, an uncharged donor is one which does not bear an electric charge.

Preference is given to monocyclopentadienyl complexes which comprise the following structural feature of the formula $(Cp)(-Z-A)_mM$ (I), where the variables have the following meanings:

Cp is a cyclopentadienyl system,

Z is a divalent bridge between A and Cp selected from the group consisting of

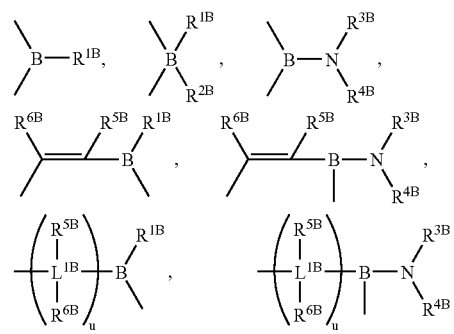

where $L^{1B}$ are each, independently of one another, carbon or silicon, $R^{1B}$–$R^{6B}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{7B}_3$, where the organic radicals $R^{1B}$–$R^{6B}$ may also be substituted by halogens and two geminal or vicinal radicals $R^{1B}$–$R^{6B}$ may also be joined to form a five-or six-membered ring and $R^{7B}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl radical and 6–20 carbon atoms in the aryl radical and two radicals $R^{7B}$ may also be joined to form a five- or six-membered ring, u is 1, 2 or 3

A is an uncharged donor group containing one or more atoms of group 15 and/or 16 of the Periodic Table of the Elements, preferably an unsubstituted, substituted or fused heteroaromatic ring system, M is a metal selected from the group consisting of titanium in the oxidation state 3, vanadium, chromium, molybdenum and tungsten and m is 1, 2 or 3.

We have also found a catalyst system comprising the monocyclopentadienyl complexes of the present invention, the use of the monocyclopentadienyl complexes or of the catalyst system for the polymerization or copolymerization of olefins and a process for preparing polyolefins by polymerization or copolymerization of olefins in the presence of the monocyclopentadienyl complex or the catalyst system and polymers obtainable in this way.

The monocyclopentadienyl complexes of the present invention comprise the structural element of the formula $(Cp)(-Z-A)_mM$ (I), where the variables are as defined above. Further ligands can therefore be bound to the metal atom M. The number of further ligands depends, for example, on the oxidation state of the metal atom. These further ligands are not additional cyclopentadienyl systems. Suitable ligands are monoanionic and dianionic ligands as are described, for example, for X. In addition, Lewis bases such as amines, ethers, ketones, aldehydes, esters, sulfides or phosphines can also be bound to the metal center M.

Cp is a cyclopentadienyl system which may have any substitution pattern and/or be fused with one or more aromatic, aliphatic, heterocyclic or heteroaromatic rings, with 1, 2 or 3 substituents, preferably 1 substituent, being formed by the group -Z-A. The basic cyclopentadienyl skeleton itself is a $C_5$ ring system having 6π electrons in which one of the carbon atoms may also be replaced by nitrogen or phosphorus, preferably phosphorus. Preference is given to using $C_5$ ring systems without replacement by a heteroatom. It is possible, for example, for a heteroaromatic containing at least one atom from the group consisting of N, P, O and S or an aromatic to be fused onto this basic cyclopentadienyl skeleton. Here, fused-on means that the heterocycle and the basic cyclopentadienyl skeleton share two atoms, preferably carbon atoms. Preference is given to cyclopentadienyl systems Cp of the formula (II)

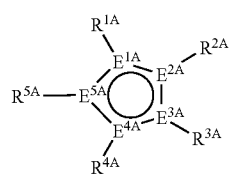

(II)

where the variables have the following meanings:

$E^{1A}$–$E^{5A}$ are each carbon or at most one $E^{1A}$ to $E^{5A}$ is phosphorus, $R^{1A}$–$R^{5A}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $NR^{6A}_2$, $N(SiR^{6A}_3)_2$, $OR^{6A}$, $OSiR^{6A}_3$, $SiR^{6A}_3$, $BR^{6A}_2$, where the organic radicals $R^{1A}$–$R^{5A}$ may also be substituted by halogens and two vicinal radicals $R^{1A}$–$R^{5A}$ may be also be joined to form a five- or six-membered ring, and/or two vicinal radicals $R^{1A}$–$R^{5A}$ are joined to form a heterocycle which contains at least one atom from the group consisting of N, P, O and S, with 1, 2 or 3 substituents, preferably 1 substituent, $R^{1A}$–$R^{5A}$ being a group -Z-A, and $R^{6A}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part and two geminal radicals $R^{6A}$ may also be joined to form a five- or six-membered ring.

In preferred cyclopentadienyl systems Cp, all $E^{1A}$ to $E^{5A}$ are carbon.

Two vicinal radicals $R^{1A}$–$R^{5A}$ in each case together with the $E^{1A}$–$E^{5A}$ bearing them may form a heterocycle, preferably a heteroaromatic, which contains at least one atom from the group consisting of nitrogen, phosphorus, oxygen and/or sulfur, particularly preferably nitrogen and/or sulfur, with the $E^{1A}$–$E^{5A}$ present in the heterocycle or heteroaromatic preferably being carbon atoms. Preference is given to heterocycles and heteroaromatics having a ring size of 5 or 6 ring atoms. Examples of 5-membered ring heterocycles, which can contain from 1 to 4 nitrogen atoms and/or one sulfur or oxygen atom as ring atoms in addition to the carbon atoms, are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole or 1,2,4-triazole. Examples of 6-membered heteroaryl groups, which may contain from one to four nitrogen atoms and/or one phosphorus atom, are pyridine, phosphabenzene, pyridazine, pyrimidine, pyrazine, 1,3,5-triazine, 1,2,4-triazine or 1,2,3-triazine. The 5-membered and 6-membered heterocycles can also be substituted by $C_1$–$C_{10}$-alkyl, $C_6$–$C_{10}$-aryl, alkylaryl having from 1 to 10 carbon atoms in the alkyl part and 6–10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole or benzimidazole. Examples of benzo-fused 6-membered heteroaryl groups are chroman, benzopyran, quinoline, isoquinoline, cinnoline, phthalazine, quinazoline, quinoxaline, 1,10-phenanthroline or quinolizine. Terminology and numbering of the heterocycles has been taken from Lettau, Chemie der Heterocyclen, 1st edition, VEB, Weinheim 1979. The heterocycles/heteroaromatics are preferably fused to the basic cyclopentadienyl skeleton via a C—C double bond of the heterocycle/heteroaromatic. Heterocycles/heteroaromatics having one heteroatom are preferably 2,3-fused or b-fused.

Examples of cyclopentadienyl systems Cp having a fused-on heterocycle are thiapentalene, 2-methylthiapentalene, 2-ethylthiapentalene, 2-isopropylthiapentalene, 2-n-butylthiapentalene, 2-tert-butylthiapentalene, 2-trimethylsilylthiapentalene, 2-phenylthiapentalene, 2-naphthylthiapentalene, 3-methylthiapentalene, 4-phenyl-2,6-dimethyl-1-thiapentalene, 4-phenyl-2,6-diethyl-1-thiapentalene, 4-phenyl-2,6-diisopropyl-1-thiapentalene, 4-phenyl-2,6-di-n-butyl-1-thiapentalene, 4-phenyl-2,6-di-trimethylsilyl-1-thiapentalene, azapentalene, 2-methylazapentalene, 2-ethylazapentalene, 2-isopropylazapentalene, 2-n-butylazapentalene, 2-trimethylsilylazapentalene, 2-phenylazapentalene, 2-naphthylazapentalene, 1-phenyl-2,5-dimethyl-1-azapentalene, 1-phenyl-2,5-diethyl-1-azapentalene, 1-phenyl-2,5-di-n-butyl-1-azapentalene, 1-phenyl-2, 5-di-tert-butyl-1-azapentalene, 1-phenyl-2,5-ditrimethylsilyl-1-azapentalene, 1-tert-butyl-2,5-dimethyl-1-azapentalene, oxapentalene, phosphapentalene, 1-phenyl-2,5-dimethyl-1-phosphapentalene, 1-phenyl-2,5-diethyl-1-phosphapentalene, 1-phenyl-2,5-di-n-butyl-1-phosphapentalene, 1-phenyl-2,5-di-tert-butyl-1-phosphapentalene, 1-phenyl-2,5-di-trimethylsilyl-1-phosphapentalene, 1-methyl-2,5-dimethyl-1-phosphapentalene, 1-tert-butyl-2,5-dimethyl-1-phosphapentalene, 7-cyclopenta-[1,2]thioeno[3,4]cyclopentadiene or 7-cyclopenta[1,2]pyrrolo[3,4]cyclopentadiene.

In further, preferred cyclopentadienyl systems Cp, four of the radicals $R^{1A}$–$R^{5A}$, i.e. two pairs of vicinal radicals, form two heterocycles, in particular heteroaromatics. The heterocyclic systems are the same as those indicated above. Examples of cyclopentadienyl systems Cp having two fused-on heterocycles are 7-cyclopentadithiophene, 7-cyclopentadipyrrole or 7-cyclopentadiphosphole.

The synthesis of such cyclopentadienyl systems having a fused-on heterocycle is described, for example, in the abovementioned WO 98/22486. In "Metalorganic catalysts for synthesis and polymerisation", Springer Verlag 1999, p. 150 ff, Ewen et al. describe further syntheses of these cyclopentadienyl systems.

The polymerization behavior of the metal complexes can likewise be influenced by variation of the substitutuents $R^{1A}$–$R^{5A}$. The number and type of substituents can influence the ability of olefins to be polymerized to gain access to the metal atom M. In this way, the activity and selectivity of the catalyst in respect of various monomers, in particular bulky monomers, can be modified. Since the substituents can also influence the rate of termination reactions of the growing polymer chain, the molecular weight of the polymers formed can also be altered in this way. The chemical structure of the substituents $R^{1A}$ to $R^{5A}$ can therefore be varied within a wide range in order to achieve the desired results and to obtain a tailored catalyst system. Possible carboorganic substituents $R^{1A}$–$R^{5A}$ are, for example: $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$–$C_{10}$-aryl group as substituent, e.g. cyclopropyl, cyclobutyl, cyclopentyl, cyclohexyl, cycloheptyl, cyclooctyl, cyclononyl or cyclododecyl, $C_2$–$C_{20}$-alkenyl which may be linear, cyclic or branched and can have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, with two $R^{1A}$ to $R^{5A}$ also being able to be joined to form a 5- or 6-membered ring and the organic radicals $R^{1A}$–$R^{5A}$ also being able to be substituted by halogens such as fluorine, chlorine or bromine. Furthermore, $R^{1A}$–$R^{5A}$ can be amino or alkoxyl, for example dimethylamino, N-pyrrolidinyl, picolinyl, methoxy, ethoxy or isopropoxy. In organosilicon substituents $SiR^{6A}_3$, $R^{6A}$ can be the same radicals as indicated above for $R^{1A}$–$R^{5A}$, and two $R^{6A}$ may also be joined to form a 5- or 6-membered ring, e.g. trimethylsilyl, triethylsilyl, butyidimethylsilyl, tributylsilyl, tri-tert-butylsilyl, triallylsilyl, triphenylsilyl or dimethylphenylsilyl. These $SiR^{6A}_3$ radicals may also be bound to the basic cyclopentadienyl skeleton via an oxygen or nitrogen atom, for example trimethylsilyloxy, triethylsilyloxy, butyidimethylsilyloxy, tributylsilyloxy or tri-tert-butylsilyloxy. Preferred radicals are $R^{1A}$–$R^{5A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl and anthranyl. As organosilicon substituents, particular preference is given to trialkylsilyl groups having from 1 to 10 carbon atoms in the alkyl radical, in particular trimethylsilyl groups.

Examples of such cyclopentadienyl systems (without the group -Z-A, which is preferably located in the 1 position) are 3-methylcyclopentadienyl, 3-ethylcyclopentadienyl, 3-isopropylcyclopentadienyl, 3-tert-butylcyclopentadienyl, dialkylcyclopentadienyl such as tetrahydroindenyl, 2,4-dimethylcyclopentadienyl or 3-methyl-5-tert-butylcyclopentadienyl, trialkylcyclopentadienyl such as 2,3,5-trimethylcyclopentadienyl or tetraalkylcyclopentadienyl such as 2,3,4,5-tetramethylcyclopentadienyl.

Furthermore, preference is also given to compounds in which two vicinal radicals $R^{1A}$–$R^{5A}$ form a cyclic fused-on ring system, i.e. together with the $E^{1A}$–$E^{5A}$ skeleton, preferably a $C_5$-cyclopentadienyl skeleton, form, for example, an unsubstituted or substituted indenyl, benzindenyl, phenanthrenyl, fluorenyl or tetrahydroindenyl system, for example indenyl, 2-methylindenyl, 2-ethylindenyl, 2-isopropylindenyl, 3-methylindenyl, benzindenyl or 2-methylbenzindenyl.

The fused ring system can bear further $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $NR^{6A}_2$, $N(SiR^{6A}_3)_2$, $OR^{6A}$, $OSiR^{6A}_3$ or $SiR^{6A}_3$ groups, e.g. 4-methylindenyl, 4-ethylindenyl, 4-isopropylindenyl, 5-methylindenyl, 4-phenylindenyl, 5-methyl-4-phenylindenyl, 2-methyl-4-phenylindenyl or 4-naphthylindenyl.

Preferred substituents $R^{1A}$–$R^{5A}$ which do not form -Z-A are the carboorganic substituents described above and the carboorganic substituents which form a cyclic fused-on ring system, in particular their preferred embodiments.

m can be 1, 2 or 3, i.e. 1, 2 or 3 radicals $R^{1A}$–$R^{5A}$ are -Z-A; if 2 or 3 -Z-A radicals are present, these can be identical or different. Preference is given to only one of the radicals $R^{1A}$–$R^{5A}$ being -Z-A (m=1).

As in the case of the metallocenes, the monocyclopentadienyl complexes of the present invention can be chiral. Thus, one of the substituents $R^{1A}$–$R^{5A}$ on the basic cyclopentadienyl skeleton can have one or more chiral centers or else the cyclopentadienyl system Cp can itself be enantiotopic so that chirality is induced only when it is bound to the transition metal M (for formalisms regarding the chirality of cyclopentadienyl compounds, see R. Halterman, Chem. Rev. 92, (1992), 965–994).

Possible carboorganic substituents $R^{1B}$–$R^{6B}$ on the link Z are, for example, the following: hydrogen, $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$–$C_{10}$-aryl group as substituent, e.g. cyclopropyl, cyclobutyl, cyclopentyl, cyclohexyl, cycloheptyl, cyclooctyl, cyclononyl or cyclododecyl, $C_2$–$C_{20}$-alkenyl which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$–$C_{20}$-aryl which may bear further alkyl groups as substituents, e.g., phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl, which may bear further alkyl groups as substituents, e.g. benzyl, o-, m-, p-methylbenzyl, 1- or 2-ethylphenyl, with two $R^{1B}$ to $R^{6B}$ also being able to be joined to form a 5- or 6-membered ring, for example cyclohexane, and the organic radicals $R^{1B}$–$R^{6B}$ also being able to be substituted by halogens such as fluorine, chlorine or bromine, for example pentafluorophenyl or bis-3,5-trifluoromethylphen-1-yl, and alkyl or aryl.

In organosilicon substituents $SiR^{7B}_3$, possible radicals $R^{7B}$ are the same radicals as described above for $R^{1B}$–$R^{6B}$ with two $R^{7B}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. Preferred radicals $R^{1B}$–$R^{6B}$ are hydrogen, methyl, ethyl, n-propyl, isopropyl, n-butyl, isobutyl, tert-butyl, n-pentyl, n-hexyl, n-heptyl, n-octyl, benzyl, phenyl, ortho-dialkyl- or dichloro-substituted phenyls, trialkyl- or trichloro-substituted phenyls, naphthyl, biphenyl and anthranyl.

Particularly preferred substituents $R^{1B}$ and $R^{2B}$ are $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalky which may bear further alkyl groups as substituents, e.g. benzyl, o-, m-, p-methylbenzyl, 1- or 2-ethylphenyl, with two $R^{1B}$ to $R^{2B}$ also being able to be joined to form a 5- or 6-membered ring such as cyclohexane and the organic radicals $R^{1B}$–$R^{2B}$ also being able to be substituted by halogens such as fluorine, chlorine or bromine, in particular fluorine, for example pentafluorophenyl or bis-3,5-trifluoromethylphen-1-yl, and alkyl or aryl. Particular preference is given to methyl, ethyl, 1-propyl, 2-iso-propyl, 1-butyl, 2-tert-butyl, phenyl and pentafluorophenyl. In the case of the bridges $BR^{1B}$ and $BR^{1B}R^{2B}$, particular preference is given to combinations in which at least the substituent $R^{1B}$, preferably $R^{1B}$ and $R^{2B}$ is/are a $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, and may be partially fluorinated or perfluorinated, in particular pentafluorophenyl and bis-3,5-trifluoromethylphen-1-yl.

Preferred substituents $R^{3B}$ and $R^{4B}$ are $C_1$–$C_{20}$-alkyl, which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$–$C_{10}$-aryl group as substituent, e.g. cyclopropyl, cyclobutyl, cyclopentyl, cyclohexyl, cycloheptyl, cyclooctyl, cyclononyl or cyclododecyl, $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may bear further alkyl groups as substituents, e.g. benzyl, o-, m-, p-methylbenzyl, 1- or 2-ethylphenyl, with two $R^{3B}$ to $R^{4B}$ also being able to be joined to form a 5- or 6-membered ring such as cyclohexane and may bear alkyl or aryl groups as substituents, and $SiR^{7B}_3$ as described above, e.g. trimethylsilyl, triethylsilyl, butyldimethylsilyl, tributylsilyl, tri-tert-butylsilyl, triallylsilyl, triphenylsilyl or dimethylphenylsilyl. $R^{3B}$ to $R^{4B}$ together with the nitrogen form an amide substituent. This is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tert-octylamide, dioctylamide, bis(2-ethylhexyl)amide, didecylamide, N-methyloctadecylamide, N-methylcyclohexylamide, N-ethylcyclohexylamide, N-isopropylcyclohexylamide, N-tert-butylcyclohexylamide, dicyclohexylamide, pyrrolidine, piperidine, hexamethylenimine, decahydroquinoline, diphenylamine, N-methylanilide or N-ethylanilide.

$R^{5B}$ and $R^{6B}$ are preferably hydrogen, $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may bear further alkyl groups as substituents, e.g. benzyl, o-, m-, p-methylbenzyl, 1- or 2-ethylphenyl, with two $R^{5B}$ to $R^{6B}$ also being able to be joined to form a 5- or 6-membered ring such as cyclohexane and the organic radicals $R^{5B}$–$R^{6B}$ also being able to be substituted by halogens such as fluorine, chlorine or bromine, in particular fluorine, for example pentafluorophenyl or bis-3,5-trifluoromethylphen-1-yl, and alkyl or aryl. $R^{5B}$ and $R^{6B}$ together with $L^{1B}$ preferably form a group $CR^{5B}R^{6B}$, $SiR^{5B}R^{6B}$, $(CR^{5B}R^{6B})_2$, $CR^{5B}R^{6B}SiR^{5B}R^{6B}$ or $(SiR^{5B}R^{6B})_2$, in particular $CR^{5B}R^{6B}$. Here, the preferred substituents $R^{5B}$ and $R^{6B}$ described above are likewise preferred embodiments. $CR^{5B}R^{6B}$ is particularly preferably a $CHR^{6B}$ or $CH_2$ group. The group $L^{1B}R^{5B}R^{6B}$ may be bound to the cyclopentadienyl system or to A. Preference is given to the group $L^{1B}R^{5B}R^{6B}$ or its preferred embodiments being bound to A.

The bridge Z between the cyclopentadienyl system Cp and the uncharged donor A is a divalent organic bridge comprising a boron-containing group and/or carbon and/or silicon bridge elements. Z can be bound to the basic cyclopentadienyl skeleton or to the heterocycle or the fused-on ring of the cyclopentadienyl system. Z is preferably bound to the cyclopentadienyl skeleton. The activity of the catalyst can be influenced by a change in the length of the linkage between the cyclopentadienyl system and A. u can be 1, 2 or 3. u is preferably 1. Very particular preference is given to Z being bound to the cyclopentadienyl skeleton next to the fused-on heterocycle or fused-on aromatic. Thus, if the heterocycle or aromatic is fused onto the basic cyclopentadienyl skeleton in the 2,3 position, then Z is preferably located in the 1 or 4 position of the cyclopentadienyl skeleton.

Preferred bridges Z are $BR^{1B}$, $BNR^{3B}R^{4B}$, $C(R^{5B}R^{6B})$—$BR^{1B}$ and $C(R^{5B}R^{6B})$—$BNR^{3B}$ $R^{4B}$. The above described embodiments and preferred embodiments of $R^{1B}$–$R^{6B}$ and $R^{7B}$ also apply to these preferred monocyclopentadienyl complexes. If Z is $BR^{1B}R^{2B}$, then B carries a negative charge which can be balanced, for example, by a positive charge on M.

A is an uncharged donor containing an atom of group 15 or 16 of the Periodic Table, preferably one or more atoms selected from the group consisting of oxygen, sulfur, nitrogen and phosphorus, preferably nitrogen and phosphorus. The donor function in A can bind intermolecularly or intramolecularly to the metal M. The donor A is preferably bound intramolecularly to M. Possible donors are uncharged functional groups which contain an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide or unsubstituted, substituted or fused, heterocyclic ring systems. A can be bound to the cyclopentadienyl radical and Z by, for example, a synthesis analogous to that described in WO 00/35928.

A is preferably a group selected from among —$OR^{1C}$, —$SR^{1C}$, —$NR^{1C}R^{2C}$, —$PR^{1C}R^{2C}$, —C=$NR^{1C}$ and unsubstituted, substituted or fused heteroaromatic ring systems, in particular —$NR^{1C}R^{2C}$, —C=$NR^{1C}$ and unsubstituted, substituted or fused heteroaromatic ring systems. $R^{1C}$ and $R^{2C}$ are each, independently of one another, hydrogen, $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$–$C_{10}$-aryl group as substituent, e.g. cyclopropyl, cyclobutyl, cyclopentyl, cyclohexyl, cycloheptyl, cyclooctyl, cyclononyl or cyclododecyl, $C_2$–$C_{20}$-alkenyl which may be linear, cyclic or branched and may have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$–$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6-or 3,4,5-trimethyl phen-1-yl, alkylaryl having from 1 to 10 carbon atoms in the alkyl part and 6–20 carbon atoms in the aryl part which may bear further alkyl groups as substituents, e.g. benzyl, o-, m-, p-methyl-benzyl, 1- or 2-ethylphenyl, or $SiR^{3C}_3$, where the organic radicals $R^{1C}$–$R^{2C}$ may also be substituted by halogens, e.g. fluorine, chlorine or bromine, or nitrogen-containing groups and further $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{3C}_3$ groups and two vicinal radicals $R^{1C}$–$R^{2C}$ may also be joined to form a five- or six-membered ring and $R^{3C}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl part and 6–20 carbon atoms in the aryl part and two radicals $R^{3C}$ may also be joined to form a five- or six-membered ring.

$NR^{1C}R^{2C}$ is an amide substituent. It is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tertoctylamide, dioctylamide, bis(2-ethylhexyl)amide, didecylamide, N-methyloctadecylamide, N-methylcyclohexylamide, N-ethylcyclohexylamide, N-isopropylcyclohexylamide, N-tert-butylcyclohexylamide, dicyclohexylamide, pyrrolidine, piperidine, hexamethylenimine, decahydroquinoline, diphenylamine, N-methylanilide or N-ethylanilide.

In the imino group —C=$NR^{1C}$, $R^{1C}$ is preferably a $C_6$–$C_{20}$ aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl.

A is preferably an unsubstituted, substituted or fused heteroaromatic ring system which may contain heteroatoms from the group consisting of oxygen, sulfur, nitrogen and phosphorus in addition to the ring carbons. Examples of 5-membered heteroaryl groups, which may contain from 1 to 4 nitrogen atoms or from 1 to 3 nitrogen atoms and/or a sulfur or oxygen atom as ring atoms in addition to the carbon atoms, are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which can contain from 1 to 4 nitrogen atoms and/or a phosphorus atom, are 2-pyridinyl, 2-phosphabenzenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The 5-membered and 6-membered heteroaryl groups may also be substituted by $C_1$–$C_{10}$-alkyl, $C_6$–$C_{10}$-aryl, alkylaryl having from 1 to 10 carbon atoms in the alkyl part and 6–10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl or 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl.

Among these heteroaromatic systems, particular preference is given to unsubstituted, substituted and/or fused six-membered heteroaromatics having 1, 2, 3, 4 or 5 nitrogen atoms in the heteroaromatic part which is bound to Z, in particular substituted and unsubstituted 2-pyridyl or 2-quinolyl. A is therefore preferably a group of the formula (III)

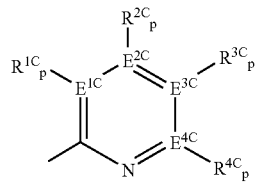

where $E^{1C}$–$E^{4C}$ are each carbon or nitrogen, $R^{1C}$–$R^{4C}$ are each, independently of one another, hydrogen, $C_1$–$C_{20}$-alkyl, $C_2$–$C_{20}$-alkenyl, $C_6$–$C^{20}$-aryl, alkylaryl having from 1 to 10 carbon atoms in the alkyl part and 6–20 carbon atoms in the aryl part or $SiR^{5C}_3$, where the organic radicals $R^{1C}$–$R^{4C}$ may also be substituted by halogens or nitrogen and further $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{5C}_3$ groups and two vicinal radicals $R^{1C}$–$R^{4C}$ or $R^{1C}$ and Z may also be joined to form a five- or six-membered ring and $R^{5C}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl part and 6–20 carbon atoms in the aryl part and two radicals $R^{5C}$ may also be joined to form a five- or six-membered ring and p is 0 when $E^{1C}$–$E^{4C}$ is nitrogen and 1 when $E^{1C}$–$^{4C}$ is carbon.

In particular, 0 or 1 $E^{1C}$–$^{4C}$ is nitrogen and the others are carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

In a preferred monocyclopentadienyl complex, the cyclopentadienyl system Cp and -Z-A form a ligand (Cp-Z-A) of the formula IV:

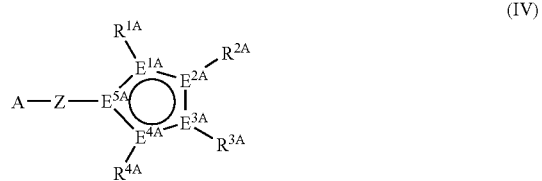

(IV)

where the variables A, Z, $E^{1A}$ to $E^{5A}$ and $R^{6A}$ are as defined above and preference is also given to their preferred embodiments and $R^{1A}$–$R^{4A}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $NR^{6A}_2$, $N(SiR^{6A}_3)_2$, $OR^{6A}$, $OSiR^{6A}_3$, $SiR^{6A}_3$, where the organic radicals $R^{1A}$–$R^{4A}$ may also be substituted by halogens and two vicinal radicals $R^{1A}$–$R^{4A}$ may also be joined to form a five- or six-membered ring, and/or two vicinal radicals $R^{1A}$–$R^{4A}$ are joined to form a heterocycle containing at least one atom from the group consisting of N, P, O and S.

The embodiments and preferred embodiments described above likewise apply to $R^{1A}$–$R^{4A}$.

In particular, the monocyclopentadienyl complex contains the ligand (Cp-Z-A) of the formula VI in the following preferred embodiment:

Z is selected from among $BR^{1B}$, $BNR^{3B}R^{4B}$, $C(R^{5B}R^{6B})$—$BR^{1B}$ and $C(R^{5B}R^{6B})$—$BNR^{3B}R^{4B}$, where the variables $R^{1B}$–$R^{7B}$ are as defined above and their preferred embodiments are also preferred here, A is

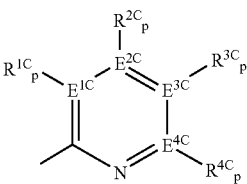

where
$E^{1C}$–$E^{4C}$ are each carbon or nitrogen,
$R^{1C}$–$R^{4C}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{5C}_3$, where the organic radicals $R^{1C}$–$R^{4C}$ may also be substituted by halogens and further $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{5c}_3$ groups and two vicinal radicals $R^{1C}$–$R^{4C}$ or $R^{1C}$ and Z may also be joined to form a five- or six-membered ring, $R^{5C}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl part and 6–20 carbon atoms in the aryl part and two radicals $R^{5C}$ may also be joined to form a five- or six-membered ring and p is 0 when $E^{1C}$–$E^{4C}$ is nitrogen and 1 when $E^{1C}$–$E^{4C}$ is carbon.

M is a metal selected from the group consisting of titanium in the oxidation state 3, vanadium, chromium, molybdenum and tungsten, preferably titanium in the oxidation state 3 and chromium. Particular preference is given to chromium in the oxidation states 2, 3 and 4, in particular 3. The metal complexes, in particular the chromium complexes can be obtained in a simple manner by reacting the appropriate metal salts, e.g. metal chlorides, with the ligand anion (e.g. using a method analogous to the examples in DE 197 10615).

Among the monocyclopentadienyl complexes according to the present invention, preference is given to those of the formula $(Cp)(-Z-A)_m MX_k$ (V), where the variables Cp, Z, A, m and M are as defined above and their preferred embodiments are also preferred here and:

X are each, independently of one another, fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 carbon atoms in the alky part and 6–20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or a bulky noncoordinating anion, $R^1$–$R^2$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $SiR^3_3$, where the organic radicals $R^1$–$R^2$ may also be substituted by halogens or nitrogen- and oxygen-containing groups and two radicals $R^1$–$R^2$ may also be joined to form a five- or six-membered ring, $R^3$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part and two radicals $R^3$ may also be joined to form a five- or six-membered ring and k is 1, 2, or 3.

The embodiments and preferred embodiments of Cp, Z, A, m and M indicated above also apply individually and in combination to these preferred monocyclopentadienyl complexes.

The ligands X are determined, for example, by the choice of the metal starting compounds used for the synthesis of the monocyclopentadienyl complexes, but can also be varied afterwards. Possible ligands X are, in particular, the halogens such as fluorine, chlorine, bromine or iodine, in particular chlorine. Alkyl radicals such as methyl, ethyl, propyl, butyl, vinyl, allyl, phenyl or benzyl are also advantageous ligands X. As further ligands X, mention may be made, purely by way of example and not implying any limitation, of trifluoroacetate, $BF_4^-$, $PF_6^-$ and weakly coordinating or noncoordinating anions (cf., for example, S. Strauss in Chem. Rev. 1993, 93, 927–942), such as $B(C_6F_5)_4^-$.

Amides, alkoxides, sulfonates, carboxylates and β-diketonates are also particularly useful ligands X. Variation of the radicals $R^1$ and $R^2$ enables, for example, fine adjustments in physical properties such as solubility to be made. Suitable carboorganic substituents $R^1$–$R^2$ are, for example, the following: $C_1$–$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl; n-decyl or n-dodecyl, 5- to 7-membered cycloalkyl which may in turn bear a $C_6$–$C_{10}$-aryl group as substituent, e.g. cyclopropyl, cyclobutyl, cyclopentyl, cyclohexyl, cycloheptyl, cyclooctyl, cyclononyl or cyclododecyl, $C_2$–$C_{20}$-alkenyl, which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$–$C_{20}$-aryl, which may bear further alkyl groups and/or N- or O-containing radicals as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl or arylalkyl which may bear further alkyl groups as substituents, e.g. benzyl, o-, m-, p-methylbenzyl, 1- or 2-ethylphenyl, where $R^1$ may also be joined to $R^2$ to form a 5- or 6-membered ring and the organic radicals $R^1$–$R^2$ may also be substituted by halogens such as fluorine, chlorine or bromine. Possible radicals $R^3$ in organosilicon substituents $SiR^3_3$ are the same radicals as described above for $R^1$–$R^2$, with two $R^3$ also being able to be joined to form a 5- or 6-membered ring, e.g. trimethylsilyl, triethylsilyl, butyidimethylsilyl, tributylsilyl, triallylsilyl, triphenylsilyl or dimethylphenylsilyl. Preference is given to using $C_1$–$C_{10}$-alkyl such as methyl, ethyl, n-propyl, n-butyl, tert-butyl, n-pentyl, n-hexyl, n-heptyl, n-octyl, and also vinyl, allyl, benzyl and phenyl as radicals $R^1$ and $R^2$. Some of these substituted ligands X are very particularly preferably used since they are obtainable from cheap and readily available starting materials. In a particularly preferred embodiment, therefore, X is dimethylamide, methoxide, ethoxide, isopropoxide, phenoxide, naphthoxide, triflate, p-toluenesulfonate, acetate or acetylacetonate.

The number k of ligands X depends on the oxidation state of the transition metal M. The number k can thus not be specified in general terms. The oxidation state of the transition metals M in catalytically active complexes is usually known to those skilled in the art. Chromium, molybdenum and tungsten are very probably present in the oxidation state +3, vanadium in the oxidation state +3 or +4. However, it is also possible to use complexes whose oxidation state does not correspond to that of the active catalyst. Such complexes can then be appropriately reduced or oxidized by means of suitable activators. Preference is given to using chromium complexes in the oxidation state +3 and titanium complexes in the oxidation state 3.

The monocyclopentadienyl complexes of the present invention can be used alone or together with further components as catalyst systems for olefin polymerization. Furthermore, we have found catalyst systems for olefin polymerization comprising A) at least one monocyclopentadienyl complex according to the present invention, B) optionally, an organic or inorganic support, C) optionally, one or more activating compounds, D) optionally, one or more catalysts suitable for olefin polymerization and E) optionally, one or more metal compounds containing a metal of group 1, 2 or 13 of the Periodic Table.

Thus, more than one of the monocyclopentadienyl complexes of the present invention can simultaneously be brought into contact with the olefin or olefins to be polymerized. This has the advantage that a wider range of polymers can be produced in this way. For example, bimodal products can be prepared in this way.

For the monocyclopentadienyl complexes of the present invention to be able to be used in polymerization processes in the gas phase or in suspension, it is often advantageous to use the metallocenes in the form of a solid, i.e. for them to be applied to a solid support B). Furthermore, the supported monocyclopentadienyl complexes have a high productivity. The monocyclopentadienyl complexes of the present invention can therefore also, if desired, be immobilized on an organic or inorganic support B) and used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polar functionalized polymers, e.g. copolymers of ethene and acrylic esters, acrolein or vinyl acetate.

Particular preference is given to a catalyst system comprising a monocyclopentadienyl complex according to the present invention and at least one activating compound C) and also a support component B).

To obtain such a supported catalyst system, the unsupported catalyst system can be reacted with a support component B). The order in which the support component B), the monocyclopentadienyl complex A) of the present invention and the activating compound C) are combined is in principle immaterial. The monocyclopentadienyl complex A) of the present invention and the activating compound C) can be fixed to the support independently of one another or simultaneously. After the individual process steps, the solid can be washed with suitable inert solvents such as aliphatic or aromatic hydrocarbons.

In a preferred method of preparing the supported catalyst system, at least one of the monocyclopentadienyl complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monocyclopentadienyl complex catalyst system is dried to ensure that all or most of the solvent has been removed from the pores of the support material. The supported catalyst is obtained as a free-flowing powder. Examples of the industrial implementation of the above process are described in WO 96/00243, WO 98/40419 or WO 00/05277. A further preferred embodiment comprises firstly applying the activating compound C) to the support component B) and subsequently bringing this supported compound into contact with the monocyclopentadienyl complex A) of the present invention.

As support component B), preference is given to using finely divided supports which can be any organic or inorganic solids. In particular, the support component B) can be a porous support such as talc, a sheet silicate such as montmorillonite, mica, an inorganic oxide or a finely divided polymer powder (e.g. a polyolefin or a polymer having polar functional groups).

The support materials used preferably have a specific surface area in the range from 10 to 1000 m²/g, a pore volume in the range from 0.1 to 5 ml/g and a mean particle size of from 1 to 500 μm. Preference is given to supports having a specific surface area in the range from 50 to 700 m²/g, a pore volume in the range from 0.4 to 3.5 ml/g and a mean particle size in the range from 5 to 350 μm. Particular preference is given to supports having a specific surface area in the range from 200 to 550 m²/g, a pore volume in the range from 0.5 to 3.0 m²/g and a mean particle size of from 10 to 150 μm.

The inorganic support can be subjected to a thermal treatment, e.g. to remove adsorbed water. Such a drying treatment is generally carried out at from 80 to 300° C., preferably from 100 to 200° C. Drying at from 100 to 200° C. Is preferably carried out under reduced pressure and/or under a blanket of inert gas (e.g. nitrogen), or the inorganic support can be calcined at from 200 to 1000° C. to produce the desired structure of the solid and/or the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, the treatment of silica gel with $(NH_4)_2SiF_6$, $NH_4F_4$, $(NH_4)_3AlF_6$, $NH_4PF_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, $AlPO_4$, $ZrO_2$, $TiO_2$, $B_2O_3$ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. These silica gels can be dried and/or calcined before use.

Further preferred supports B) are hydrotalcites and calcined hydrotalcites. In mineralogy, hydrotalcite is a natural mineral having the ideal formula $$Mg_6Al_2(OH)_{16}CO_3 \cdot 4H_2O$$

whose structure is derived from that of brucite $Mg(OH)_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula $$M(II)_{2x}^{2+}M(III)_2^{3+}(OH)_{4x+4} \cdot A_{2/n}^{n-} \cdot zH_2O$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or $B(OH)_4^-$ or polyoxo metal anions such as $Mo_7O_{24}^{6-}$ or $V_{10}O_{28}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1000° C., in particular from 400° C. to 700° C. It is possible for air or inert gas to be passed over the solid during calcination or for a vacuum to be applied.

On heating, the natural or synthetic hydrotalcites firstly give off water, i.e. drying occurs. On further heating, the actual calcination, the metal hydroxides are converted into the metal oxides by elimination of hydroxyl groups and interstitial anions; OH groups or interstitial anions such as carbonate can also still be present in the calcined hydrotalcites. A measure of this is the loss on ignition. This is the weight loss experienced by a sample which is heated in two steps firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter D50 of from 5 to 200 μm, preferably from 10 to 150 μm, particularly preferably from 15 to 100 μm and in particular from 20 to 70 μm, and usually have pore volumes of from 0.1 to 10 cm$^3$/g, preferably from 0.2 to 5 cm$^3$/g, and specific surface areas of from 30 to 1000 m$^2$/g, preferably from 50 to 800 m$^2$/g and in particular from 100 to 600 m$^2$/g. The monocyclopentadienyl complexes of the present invention are preferably applied in such an amount that the concentration of monocyclopentadienyl complexes in the finished catalyst system is from 5 to 200 μmol, preferably from 20 to 100 μmol and particularly preferably from 25 to 70 μmol per g of support B).

Some of the monocyclopentadienyl complexes of the present invention have little polymerization activity on their own and are then brought into contact with an activator, viz. the component C), to be able to display good polymerization activity. For this reason, the catalyst system optionally further comprises, as component C), one or more activating compounds, preferably at least one cation-forming compound C).

Suitable compounds C) which are able to react with the monocyclopentadienyl complex A) to convert it into a catalytically active, or more active, compound are, for example, compounds such as an aluminoxane, a strong uncharged Lewis acid, an ionic compound having a Lewis-acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formulae (X) or (XI)

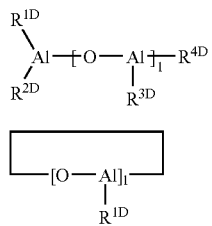

(X)

(XI)

where
R$^{1D}$–R$^{4D}$ are each, independently of one another, a C$_1$–C$_6$-alkyl group, preferably a methyl, ethyl, butyl or isobutyl group, and l is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that l is to be regarded as a mean. The aluminoxane compounds can also be present in a mixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formulae (FX) or (FXI).

It has been found to be advantageous to use the monocyclopentadienyl complexes A) and the aluminoxane compounds in such amounts that the atomic ratio of aluminum from the aluminoxane compounds including any aluminum alkyl still present to the transition metal from the monocyclopentadienyl complex A) is in the range from 1:1 to 1000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monocyclopentadienyl complex A) is usually in the range from 1:1 to 100:1, preferably from 10:1 to 50:1 and in particular in the range from 20:1 to 40:1. Preference is given to using a monocyclopentadienyl metal dialkyl compound A).

As strong, uncharged Lewis acids, preference is given to compounds of the formula (XII)

(XII)

where
M$^{2D}$ is an element of group 13 of the Periodic Table of the Elements, in particular B, Al or Ga, preferably B,
X$^{1D}$, X$^{2D}$ and X$^{3D}$ are each hydrogen, C$_1$–C$_{10}$-alkyl, C$_{6-15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which X$^{1D}$, X$^{2D}$ and X$^{3D}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl.

Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2, 2',3,3',4,4',5,5',6,6'-nonafluorobiphenyl, triethylaluminum/pentafluorophenol and triisobutylaluminum/pentafluorophenol and triethylaluminum/4,4'-dihydroxy-2, 2',3,3',5,5',6,6'-octafluorobiphenyl hydrate.

In further suitable aluminum and boron compounds of the formula (XII), $R^{1D}$ is an OH group. Examples of compounds of this type are boronic acids and borinic acids, in particular borinic acids having perfluorinated aryl radicals, for example $(C_6F_5)_2BOH$.

Strong uncharged Lewis acids suitable as actvating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

The suitable ionic compounds having Lewis acid cations include salt-like compounds of the cation of the formula (XIII)

$$[((M^{3D})^{a+})Q_1Q_2 \ldots Q_z]^{d+} \quad (XIII)$$

where $M^{3D}$ is an element of groups 1 to 16 of the Periodic Table of the Elements, $Q_1$ to $Q_z$ are singly negatively charged groups such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$–$C_{10}$-cycloalkyl which may bear $C_1$–$C_{10}$-alkyl groups as substituents, halogen, $C_1$–$C_{28}$-alkoxy, $C_6$–$C_{15}$-aryloxy, silyl or mercaptyl groups, a is an integer from 1 to 6 and z is an integer from 0 to 5, d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 97/36937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylenzylammonium tetrakis(pentafluorophenyl)borate or trityl tetrakispentafluorophenylborate.

It is also possible for two or more borate anions to be Joined to one another, as in the dianion $[(C_6F_5)_2B-C_6F_4-B(C_6F_5)_2]^{2-}$, or the borate anion can be bound via a bridge to a suitable functional group on the support surface.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents, based on the monocyclopentadienyl complex A).

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the monocyclopentadienyl complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

A likewise broad product spectrum can be achieved by use of the monocyclopentadienyl complexes A) of the present invention in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups III to XII of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl groups and ligands which are free of cyclopentadienyl groups. A large number of such compounds B) suitable for olefin polymerization are described in Chem. Rev. 2000, vol, 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene complexes. Particularly useful metallocene complexes are those of the formula (XIV)

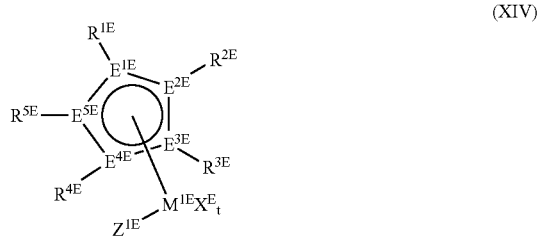

(XIV)

where the substituents and indices have the following meanings:

$M^{1E}$ is titanium, zirconium, hafnium, vanadium, niobium, tantalum, chromium, molybdenum or tungsten, or an element of group 3 of the Periodic Table and the lanthanides, $X^E$ is fluorine, chlorine, bromine, iodine, hydrogen, $C_1$–$C_{10}$-alkyl, $C_2$–$C_{10}$-alkenyl, $C_6$–$C_{15}$-aryl, alkylaryl having from 1 to 10 carbon atoms in the alkyl part and from 6 to 20 carbon atoms in the aryl part, —$OR^{6E}$ or —$NR^{6E}R^{7E}$, or two radicals $X^E$ form a substituted or unsubstituted diene ligand, in particular a 1,3-diene ligand, and the radicals $X^E$ are identical or different and may be joined to one another, $E^{1E}$–$E^{5E}$ are each carbon or not more than one $E^{1E}$ to $E^{5E}$ is phosphorus or nitrogen, preferably carbon, t is 1, 2 or 3 and is such that, depending on the valency of $M^{1E}$, the metallocene complex of the formula (FXIV) is uncharged, where $R^{6E}$ and $R^{7E}$ are each $C_1$–$C_{10}$-alkyl, $C_6$–$C_{15}$-aryl, alkylaryl, arylalkyl, fluoroalkyl or fluoroaryl, each having from 1 to 10 carbon atoms in the alkyl radical and from 6 to 20 carbon atoms in the aryl radical, and $R^{1E}$ to $R^{5E}$ are each, independently of one another, hydrogen, $C_1$–$C_{22}$-alkyl, 5- to 7-membered cycloalkyl or cycloalkenyl which may in turn bear $C_1$–$C_{10}$-alkyl groups as substituents, $C_2$–$C_{22}$-alkenyl, $C_6$–$C_{22}$-aryl, arylalkyl having from 1 to 16 carbon atoms in the alkyl part and 6–21 carbon atoms in the aryl part, $NR^{8E}_2$, $N(SiR^{8E}_3)_2$, $OR^{8E}$, $OSiR^{8E}_3$, $SiR^{8E}_3$, where the organic radicals $R^{1E}$–$R^{5E}$ may also be substituted by halogens and/or two radicals $R^{1E}$–$R^{5E}$, in particular vicinal radicals, may also be joined to form a five-, six- or seven-membered ring, and/or two vicinal radicals $R^{1E}$–$R^{5E}$ may be joined to form a five-, six- or seven-membered heterocycle which contains at least one atom from the group consisting of N, P, O and S, where $R^{8E}$ can be identical or different and are each $C_1$–$C_{10}$-alkyl, $C_3$–$C_{10}$-cycloalkyl, $C_6$–$C_{15}$-aryl, $C_1$–$C_4$-alkoxy or $C_6$–$C_{10}$-aryloxy and $Z^{1E}$ is as defined for $X^E$ or is

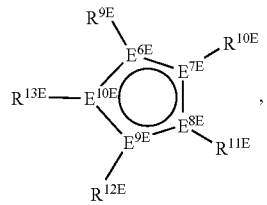

, where the radicals $R^{9E}$ to $R^{13E}$ are each, independently of one another, hydrogen, $C_1$–$C_{22}$-alkyl, 5- to 7-membered cycloalkyl or cycloalkenyl which may in turn bear $C_1$–$C_{10}$-alkyl groups as substituents, $C_2$–$C_{22}$-alkenyl, $C_6$–$C_{22}$-aryl, arylalkyl having from 1 to 16 carbon atoms in the alkyl part and 6–21 carbon atoms in the aryl part, $NR^{14E}_2$, $N(SiR^{14E}_3)_2$, $OR^{14E}$, $OSiR^{14E}_3$, $SiR^{14E}_3$, where the organic radicals $R^{9E}$–$R^{13E}$ may also be substituted by halogens and/or two radicals $R^{9E}$–$R^{13E}$, in particular vicinal radicals, may also be joined to form a five-, six- or seven-membered ring, and/or two vicinal radicals $R^{9E}$–$R^{13}E$ may be joined to form a five-, six- or seven-membered heterocycle which contains at least one atom from the group consisting of N, P, O and S, where $R^{14E}$ are identical or different and are each $C_1$–$C_{10}$-alkyl, $C_3$–$C_{10}$-cycloalkyl, $C_6$–$C_{15}$-aryl, $C_1$–$C_4$-alkoxy or $C_6$–$C_{10}$-aryloxy, $E^6$–$E^{10E}$ are each carbon or not more than one $E^{6E}$ to $E^{10E}$ is phosphorus or nitrogen, preferably carbon, or the radicals $R^{4E}$ and $Z^{1E}$ together form an —$R^{15E}_v$-$A^{1E}$- group in which $R^{15E}$ is

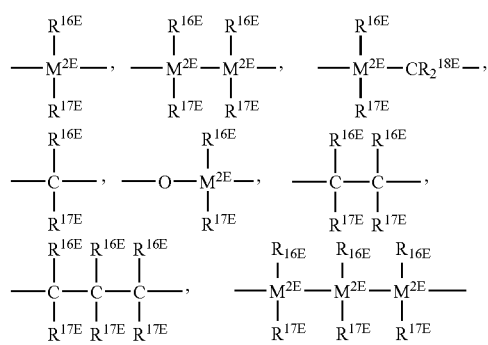

=$BR^{16E}$, =$BNR^{16E}R^{17E}$, =$AlR^{16E}$, —Ge—, —Sn—, —O—, —S—, =SO, =$SO_2$, =$NR^{16E}$, =CO, =$PR^{16E}$ or =$P(O)R^{16E}$, where $R^{16E}$, $R^{17E}$ and $R^{18E}$ are identical or different and are each a hydrogen atom, a halogen atom, a trimethylsilyl group, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_7$–$C_{15}$-alkylaryloxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or two adjacent radicals together with the atoms connecting them form a saturated or unsaturated ring having from 4 to 15 carbon atoms, and $M^{2E}$ is silicon, germanium or tin, preferably silicon, $A^{1E}$ is

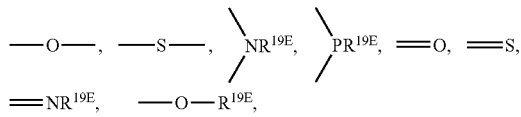

$-NR^{19E}_2$, $-PR^{19E}_2$ or an unsubstituted, substituted or fused, heterocyclic ring system, where $R^{19E}$ are each, independently of one another, $C_1-C_{10}$-alkyl, $C_6-C_{15}$-aryl, $C_3-C_{10}$-cycloalkyl, $C_7-C_{18}$-alkylaryl or $Si(R^{20E})_3$, $R^{20E}$ is hydrogen, $C_1-C_{10}$-alkyl, $C_6-C_{15}$-aryl which may in turn bear $C_1-C_4$-alkyl group as substituents or $C_3-C_{10}$-cycloalkyl, v is 1 or when $A^{1E}$ is an unsubstituted, substituted or fused, heterocyclic ring system may also be 0, or the radicals $R^{4E}$ and $R^{12E}$ together form an $-R^{15E}$-group.

$A^{1E}$ together with the bridge $R^{15E}$ can, for example, form an amine, ether, thioether or phosphine. However, $A^{1E}$ may also be an unsubstituted, substituted or fused, heterocyclic aromatic ring system which can contain heteroatoms from the group consisting of oxygen, sulfur, nitrogen and phosphorus in addition to carbon atoms in the ring. Examples of five-membered heteroaryl groups which can contain from 1 to 4 nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which can contain from 1 to 4 nitrogen atoms and/or a phosphorus atom, are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazinyl. The 5-membered and 6-membered heteroaryl groups can also be substituted by $C_1-C_{10}$-alkyl, $C_6-C_{10}$-aryl, alkylaryl having from 1 to carbon atoms in the alkyl part and 6–10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Nomenclature and numbering of the heterocycles has been taken from L. Fieser and M. Fieser, Lehrbuch der organischen Chemie, 3rd revised edition, Verlag Chemie, Weinheim 1957.

It is preferred that the radicals $X^E$ in the formula (XIV) are identical, preferably fluorine, chlorine, bromine, $C_1-C_7$-alkyl or aralkyl, in particular chlorine, methyl or benzyl.

The synthesis of such complexes can be carried out by methods known per se, preferably by reaction of the appropriately substituted, cyclic hydrocarbon anions with halides of titanium, zirconium, hafnium or chromium.

Among the metallocene complexes of the formula (XIV), preference is given to

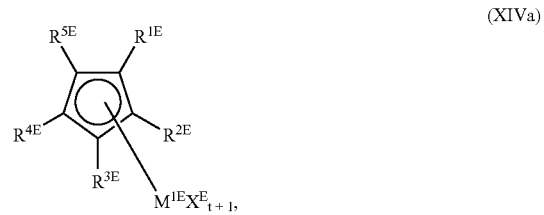

(XIVa)

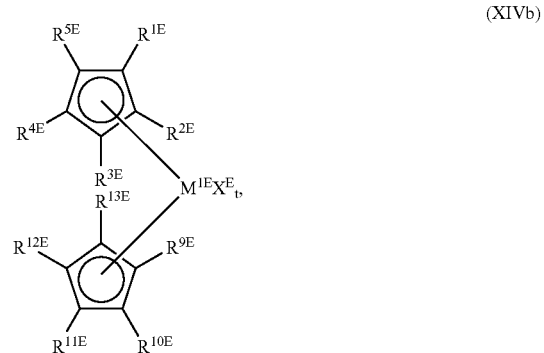

(XIVb)

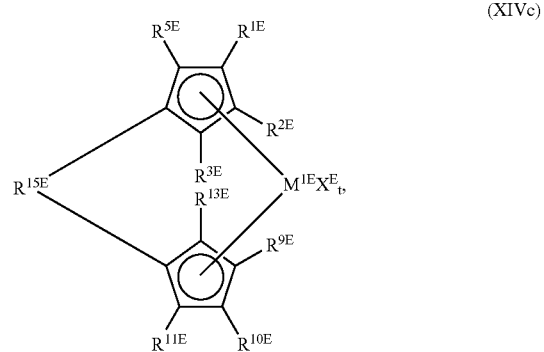

(XIVc)

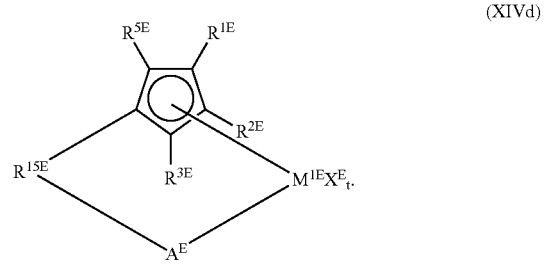

(XIVd)

Among the compounds of the formula (XIVa), particular preference is given to those in which $M^{1E}$ is titanium, vanadium or chromium, $X^E$ is chlorine, $C_1-C_4$-alkyl, phenyl, alkoxy or aryloxy, t is 1 or 2 and $R^{1E}$ to $R^{5E}$ are each hydrogen or $C_1-C_6$-alkyl or two adjacent radicals $R^{1E}$ to $R^{5E}$ form a substituted or unsubstituted benzo group.

Among the compounds of the formula (XIVb), preference is given to those in which $M^{1E}$ is titanium, zirconium, vanadium, hafnium or chromium, $X^E$ is fluorine, chlorine, $C_1$–$C_4$-alkyl or benzyl, or two radicals $X^E$ form a substituted or unsubstituted butadiene ligand, t is 0 in the case of chromium, otherwise 1 or 2, preferably 2, $R^{1E}$ to $R^{5E}$ are each hydrogen, $C_1$–$C_8$-alkyl, $C_6$–$C_8$-aryl, $NR^{8E}_2$, $OSiR^{8E}_3$ or $Si(R^{8E})_3$ and $R^{9E}$ to $R^{13E}$ are each hydrogen, $C_1$–$C_8$-alkyl or $C_6$–$C_8$-aryl, $NR^{14E}_2$, $OSiR^{14E}_3$ or $Si(R^{14E})_3$ or two radicals $R^1$ to $R^5$ and/or $R^9$ to $R^{13}$ together with the $C_5$ ring form an indenyl or substituted indenyl system.

The compounds of the formula (XIVb) in which the cyclopentadienyl radicals are identical are particularly useful.

Examples of particularly useful compounds D) of the formula (XIVb) include: bis(cyclopentadienyl)zirconium dichloride, bis(pentamethylcyclopentadienyl)zirconium dichloride, bis(methylcyclopentadienyl)zirconium dichloride, bis(ethylcyclopentadienyl)zirconium dichloride, bis(n-butylcyclopentadienyl)zirconium dichloride, bis(1-n-butyl-3-methylcyclopentadienyl)zirconium dichloride, bis (indenyl)zirconium dichloride, bis(tetrahydroindenyl) zirconium dichloride and bis (trimethylsilylcyclopentadienyl)zirconium dichloride and also the corresponding dimethylzirconium compounds.

Particularly useful compounds of the formula (XIVc) are those in which $R^{15E}$ is

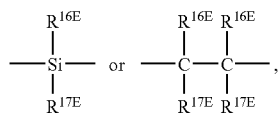

or $=BR^{16E}$ or $=BNR^{16E}R^{17E}$, $M^{1E}$ is titanium, zirconium or hafnium, in particular zirconium, and $X^E$ are identical or different and are each chlorine, $C_1$–$C_4$-alkyl, benzyl, phenyl or $C_7$–$C_{15}$-alkylaryloxy.

Particularly useful compounds of the formula (XIVc) are those of the formula (XIVc')

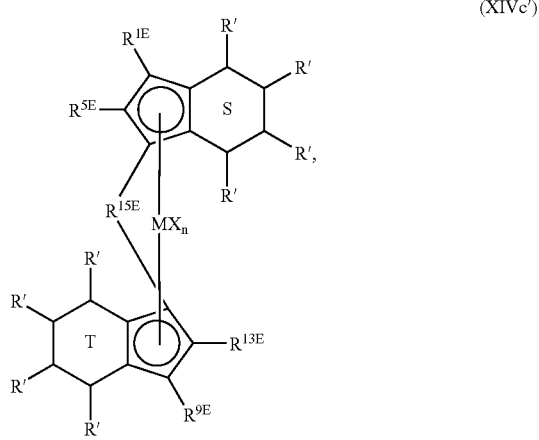

(XIVc')

where the radicals R' are identical or different and are each hydrogen, $C_1$–$C_{10}$-alkyl or $C_3$–$C_{10}$-cycloalkyl, preferably methyl, ethyl, isopropyl or cyclohexyl, $C_6$–$C_{20}$-aryl, preferably phenyl, naphthyl or mesityl, $C_7$–$C_{40}$-arylalkyl, $C_7$–$C_{40}$-alkylaryl, preferably 4-tert-butylphenyl or 3,5-di-tert-butylphenyl, or $C_{8-40}$-arylalkenyl, $R^{5E}$ and $R^{13E}$ are identical or different and are each hydrogen, $C_1$–$C_6$-alkyl, preferably methyl, ethyl, isopropyl, n-propyl, n-butyl, n-hexyl or tert-butyl, and the rings S and T may be identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6 positions, the 2,4,6 positions, the 2,5,6 positions, the 2,4,5,6 positions or the 2,4,5,6,7 positions, in particular in the 2,4 positions, with the following numbering applying to the site of substitution:

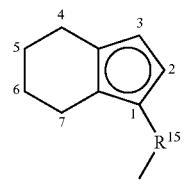

Furthermore, preference is given to using bridged bis-indenyl complexes in the rac or pseudo-rac form as component D). The term "pseudo-rac form" refers to complexes in which the two indenyl ligands are in the rac arrangement relative to one another when all other substituents of the complex are disregarded.

Further examples of particularly useful catalysts D) (XIVc) and (XIVc') include: dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis (cyclopentadienyl)zirconium dichloride, ethylenebis (indenyl)zirconium dichloride, ethylenebis (tetrahydroindenyl)zirconium dichloride, tetramethylethylene-9-fluorenyl(cyclopentadienyl)zirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(2-methylindenyl)zirconium dichloride, dimethylsilanediylbis(2-isopropylindenyl) zirconium dichloride, dimethylsilanediylbis(2-tert-butylindenyl)zirconium dichloride, diethylsilanediylbis(2-methylindenyl)zirconium dibromide, dimethylsilanediylbis (3-methyl-5-methylcyclopentadienyl)zirconium dichloride, dimethylsilanediylbis(3-ethyl-5-isopropylcyclopentadienyl) zirconium dichloride, dimethylsilanediylbis(2-ethylindenyl) zirconium dichloride, dimethylsilanediylbis(2-methyl-4,5-benzindenyl)zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis (2-methyl-4-(1-naphthyl)indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride, dimethylsilanediylbis(2-i-butyl-4-(1-naphthyl)indenyl)zirconium dichloride, dimethylsilanediylbis(2-propyl-4-(9-phenanthryl)indenyl) zirconium dichloride, dimethylsilanediylbis(2-methyl-4-isopropylindenyl)zirconium dichloride, dimethylsilanediylbis(2,7-dimethyl-4-isopropylindenyl)zirconium dichloride, dimethylsilanediylbis(2-methyl-4,6-diisopropylindenyl)zirconium dichloride, dimethylsilanediylbis(2-methyl-4[p-trifluoromethylphenyl]indenyl)zirconium dichloride, dimethylsilanediylbis(2-methyl-4-[3',5'-dimethylphenyl]indenyl) zirconium dichloride, dimethylsilanediylbis(2-methyl-4-[4'-tert-butylphenyl]indenyl)zirconium dichloride, diethylsilanediylbis(2-methyl-4-[4'-tert-butylphenyl]indenyl)zirconium dichloride, dimethylsilanediylbis(2-ethyl-4-[4'-tert-butylphenyl]indenyl)zirconium dichloride, dimethylsilanediylbis(2-propyl-4-[4'-tert-butylphenyl]-indenyl) zirconium dichloride, dimethylsilanediylbis(2-isopropyl-4-[4'-tert-butylphenyl]indenyl)zirconium dichloride, dimethylsilanediylbis(2-n-butyl-4-[4'-tert-butylphenyl]indenyl)zirconium dichloride, dimethylsilanediylbis(2-hexyl-4-[4'-tert-butylphenyl]indenyl)zirconium dichloride, dimethylsilanediyl (2-isopropyl-4-phenylindenyl)(2-methyl-4-phenylindenyl)zirconium dichloride, dimethylsilanediyl(2-isopropyl-4-(1-naphthyl)indenyl)(2-methyl-4-(1-naphthyl)indenyl) dichloride, dimethylsilanediyl(2-isopropyl)-4-[4'-tert-butylphenyl]indenyl)(2-methyl-4-[4'-tert-butylphenyl]indenyl)zirconium dichloride, dimethylsilanediyl(2-isopropyl-4-[4'-tert-butylphenyl]indenyl)(2-ethyl-4-[4'-tert -butylphenyl]indenyl)zirconium dichloride, dimethylsilanediyl(2-isopropyl-4-[4'-tert-butylphenyl]indenyl)(2-methyl-4-[3',5'-bis-tert-butylphenyl] indenyl)zirconium dichloride, dimethylsilanediyl(2-isopropyl-4-[4'-tert-butylphenyl]indenyl)(2-methyl-4-[1'-naphthyl]indenyl)zirconium dichloride and ethylene(2-isopropyl-4-[4'-tert-butylphenyl]indenyl)(2-methyl-4-[4'-tert-butylphenyl]-indenyl) zirconium dichloride, and also the corresponding dimethylzirconium, zirconium monochloride mono(alkylaryloxide) and zirconium di(alkylaryloxide) compounds. The complexes are preferably used in the rac form.

Such complexes can be synthesized by methods known per se, preferably by reaction of the appropriately substituted, cyclic hydrocarbon anions with halides of titanium, zirconium, hafnium, vanadium, niobium, tantalum or chromium. Examples of appropriate preparative methods are described, inter alia, in Journal of Organometallic Chemistry, 369 (1989), 359–370.

Particularly useful compounds of the formula (XIVd) are those in which $M^{1E}$ is titanium or zirconium, in particular titanium, and $X^E$ is chlorine, $C_1$–$C_4$-alkyl or phenyl or two radicals X form a substituted or unsubstituted butadiene ligand, $R^{15E}$ is

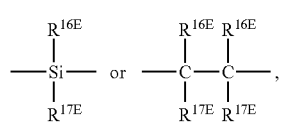

or $=BR^{16E}$ or $=BNR^{16E}R^{17E}$, $A^{1E}$ is

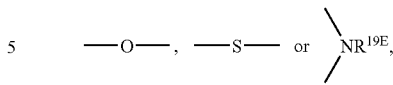

t is 1 or 2, preferably 2, $R^{1E}$ to $R^{3E}$ and $R^{5E}$ are each hydrogen, $C_1$–$C_{10}$-alkyl, preferably methyl, $C_3$–$C_{10}$-cycloalkyl, $C_6$–$C_{15}$-aryl, $NR^{8E}{}_2$ or $Si(R^8)_3$, or two adjacent radicals form a cyclic group having from 4 to 12 carbon atoms, with particular preference being given to all $R^{1E}$ to $R^{3E}$ and $R^{5E}$ being methyl. Particularly useful complexes D) of the formula (XIVd) are dimethylsilanediyl(tetramethylcyclopentadienyl)(benzylamino)titanium dichloride, dimethylsilanediyl(tetramethylcyclopentadienyl)(tert-butylamino)titanium dichloride, dimethylsilanediyl(tetramethylcyclopentadienyl)(adamantyl) titanium dichloride and dimethylsilanediyl(indenyl)(tert-butylamino)titanium dichloride.

Another group of compounds of the formula (XIVd) which are particularly useful are those in which $M^{1E}$ is titanium, vanadium or chromium, preferably in the oxidation state III, and $X^E$ is chlorine, $C_1$–$C_4$-alkyl or phenyl or two radicals $X^E$ form a substituted or unsubstituted butadiene ligand, $R^{15E}$ is

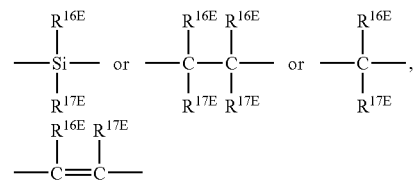

, or $=BR^{16E}$ or $=BNR^{16E}R^{17E}$, $A^{1E}$ is $-O-R^{19E}$, $-NR^{19E}{}_2$, $-PR^{19E}{}_2$ or an unsubstituted, substituted or fused, heterocyclic, in particular heteroaromatic, ring system, v is 1 or when $A^{1E}$ is an unsubstituted, substituted or fused, heterocyclic ring system may be 0 or 1, $R^{1E}$ to $R^{3E}$ and $R^{5E}$ are each hydrogen, $C_1$–$C_{10}$-alkyl, $C_3$–$C_{10}$-cycloalkyl, $C_6$–$C_{15}$-aryl or $Si(R^{8E})_3$, or two adjacent radicals form a cyclic group having from 4 to 12 carbon atoms.

In a preferred embodiment, $A^{1E}$ is an unsubstituted, substituted or fused, heteroaromatic ring system and $M^{1E}$ is chromium. Very particular preference is given to $A^{1E}$ being an unsubstituted or substituted, e.g. alkyl-substituted quinolyl or pyridyl bound in position 8 or 2, e.g. 8-quinolyl, 8-(2-methylquinolyl), 8-(2,3,4-trimethylquinolyl), 8-(2,3,4,5,6,7-hexamethylquinolyl), v being 0 and $M^{1E}$ being chromium. Preferred catalysts D) of this type are 8-quinolyl)-2-methyl-4-methylcyclo-pentadienylchromium (III) dichloride, 1-(8-quinolyl)-3-isopropyl-5-methylcyclopentadienylchromium(III) dichloride, 1-(8-quinolyl)-3-tert-butyl-5-methylcyclopentadienylchromium(III) dichloride, 1-(8-quinolyl)-2,3,4,5-tetramethylcyclopentadienylchromium (III) dichloride, 1-(8-quinolyl)tetrahydroindenylchromium (III) dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III)

dichloride, 1-(8-quinolyl)benzindenylchromium(III) dichloride, 1-(8-quinolyl)-2-methylbenzindenylchromium(III) dichloride, 1-(8-(2-methylquinolyl))-2,3,4,5-tetramethylcyclopentadienylchromium(III) dichloride, 1-(8-(2-methylquinolyl))tetrahydroindenylchromium(III) dichloride, 1-(8-(2-methylquinolyl))indenylchromium (III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) dichloride, 1-(8-(2-methylquinolyl))benzindenylchromium(III) dichloride or 1-(8-(2-methylquinolyl))-2-methylbenzindenylchromium (III) dichloride.

Furthermore, owing to the ease of preparation, preference is given to compounds in which $R^{15E}$ is CH=CH or 1,2-phenylene and $A^{1E}$ is $NR^{19E}{}_2$, and compounds in which $R^{15E}$ is $CH_2$, $C(CH_3)_2$ or $Si(CH_3)_2$ and $A^{1E}$ is unsubstituted or substituted 8-quinolyl or unsubstituted or substituted 2-pyridyl.

The preparation of such functional cyclopentadienyl ligands has been known for a long time. Various synthetic routes to these complexing ligands are described, for example, by M. Enders et al. in Chem. Ber. (1996), 129, 459–463, or P. Jutzi and U. Siemeling in J. Orgmet. Chem. (1995), 500, 175–185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed from a cyclopentadienyl or heterocyclopentadienyl and a fused-on heterocycle, with the heterocycles preferably being aromatic and containing nitrogen and/or sulfur. Such compounds are described, for example, in WO 98/22486. These are in particular dimethylsilanediyl(2-methyl-4-phenylindenyl)(2,5-dimethyl-N-phenyl-4-azapentalene)zirconium dichloride, dimethylsilanediylbis(2-methyl-4-phenyl-4-hydroazulenyl)zirconium dichloride or dimethylsilanediylbis(2-ethyl-phenyl-4-hydroazulenyl)zirconium dichloride.

Further suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5-tri(methyl)-1,3,5-triazacyclohexane]chromium trichloride, [1,3,5-tri(ethyl)-1,3,5-triazacyclohexane]chromium trichloride, [1,3,5-tri(octyl)-1,3,5-triazacyclohexane]chromium trichloride, [1,3,5-tri(dodecyl)-1,3,5-triazacyclohexane]-chromium trichloride and [1,3,5-tri(benzyl)-1,3,5-triazacyclohexane]chromium trichloride.

Further suitable catalysts D) are, for example, transition metal complexes with at least one ligand of the formulae XV to XIX,

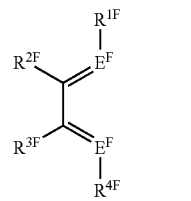

XV

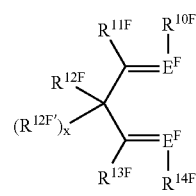

XVI

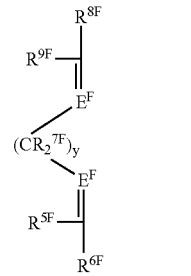

XVII

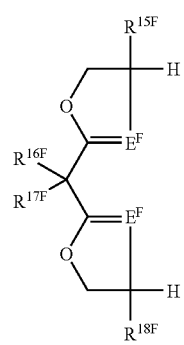

XVIII

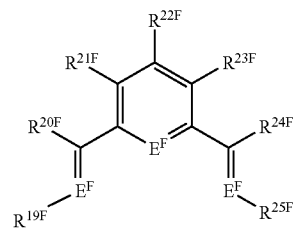

XIX where the transition metal is selected from among the elements Ti, Zr, Hf, Sc, V, Nb, Ta, Cr, Mo, W, Fe, Co, Ni, Pd, Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three atoms $E^F$ in a molecule can be identical or different.

The radicals $R^{1F}$ to $R^{25F}$, which may be identical or different within a ligand system XV to XIX, are as follows:
$R^{1F}$ and $R^{4F}$ are each, independently of one another, hydrocarbon radicals or substituted hydrocarbon radicals, preferably hydrocarbon radicals in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{3F}$ together may also form a ring system in which one or more heteroatoms may be present, $R^{6F}$ and $R^{8F}$ are each, independently of one another, hydrocarbon radicals or substituted hydrocarbon radicals, $R^{5F}$ and $R^{9F}$ are each, independently of one another, hydrogen, a hydrocarbon radical or a substituted hydrocarbon radical, where $R^{6F}$ and $R^{5F}$ or $R^{8F}$ and $R^{9F}$ may together also form a ring system, $R^{7F}$ are each, independently of one another, hydrogen, a hydrocarbon radical or a substituted hydrocarbon radical, where two $R^{7F}$ may together also form a ring system, $R^{10F}$ and $R^{14F}$ are, independently of one another, hydrocarbon radicals or substituted hydrocarbon radicals, $R^{11F}$, $R^{12F}$, $R^{12F'}$ and $R^{13F}$ are each, independently of one another, hydrogen, a hydrocarbon radical or a substituted hydrocarbon radical, where two or more geminal or vicinal radicals $R^{11F}$, $R^{12F}$, $R^{12F'}$ and $R^{13F}$ may together form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$–$C_{20}$-alkenyl, $C_6$–$C_{20}$-aryl, alkylaryl having from 1 to 10 carbon atoms in the alkyl part and 6–20 carbon atoms in the aryl part, where the organic radicals $R^{19F}$ and $R^{25F}$ may also be substituted by halogens, $R^{20}$–$R^{24F}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{26F}_3$, where the organic radicals $R^{20F}$–$R^{24F}$ may also be substituted by halogens and two vicinal radicals $R^{20F}$–$R^{24F}$ may also be joined to form a five- or six-membered ring and $R^{26F}$ are each, independently of one another, hydrogen, $C_{1-20}$-alkyl, $C_2$–$C_{20}$-alkenyl, $C_{6-20}$-aryl or alkylaryl having from 1 to 10 carbon atoms in the alkyl part and 6–20 carbon atoms in the aryl part and two radicals $R^{26F}$ may also be joined to form a five- or six-membered ring.

x is 0 or 1, with the complex of the formula (XVI) being negatively charged when x=0, and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.: Di(2,6-di-i-propylphenyl)-2,3-dimethyldiazabutadienepalladium dichloride, di(di-i-propylphenyl)-2,3-dimethyldiazabutadienenickel dichloride, di(2,6-di-i-propylphenyl)dimethyldiazabutadienedimethylpalladium, di(2,6-di-i-propylphenyl)-2,3-dimethyldiazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadiene-dimethylpalladium, di(2,6-dimethylphenyl)-2,3-dimethyldiazabutadienedimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'-bipyridylpalladium dichloride, 1,1'-bipyridyinickel dichloride, 1,1'-bipyridyl(dimethyl)palladium, 1,1'-bipyridyl(dimethyl)nickel.

Particularly useful compounds (XIX) also include those which are described in J. Am. Chem. Soc. 120, p. 4049 ff. (1998), J. Chem. Soc., Chem. Commun. 1998, 849, and WO 98/27124. $E^F$ is preferably nitrogen and $R^{19F}$ and $R^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl or 2,4,6-trimethylphenyl. At the same time, $R^{20F}$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands XIX with the transition metals Fe, Co or Ni, in particular Fe. Particular preference is given to 2,6-diacetylpyridinebis(2,4-dimethylphenylimine)iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis (2,6-diisopropylphenylimine)iron dichloride, 2,6-diacetylpyridinebis(2,4-dimethylphenylimine)cobalt dichloride, 2,6-diacetyl pyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride, and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with pi ligands having one or more heteroatoms in the pi system, for example the boratabenzene ligand, the pyrrolyl anion or the phospholyl anion, can also be used as catalysts D).

Further complexes suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one monocyclopentadienyl complex A) in the presence of at least one catalyst D) customary for the polymerization of olefins and if desired, one or more activating compounds C).

Here, depending on the catalyst combinations A) and D), one or more activating compounds C) may be advantageous. The polymerization catalysts D) can likewise be supported and can be used simultaneously or in any order with the complex A) of the present invention. For example, the monocyclopentadienyl complex A) and the polymerization catalysts D) can be applied together to a support B) or different supports B). It is also possible to use mixtures of various catalysts as component D). The molar ratio of monocyclopentadienyl complex A) to polymerization catalyst B) is usually in the range from 1:100 to 100:1, preferably from 1:20 to 20:1 and particularly preferably from 1:10 to 10:1.

The catalyst system may further comprise, as additional component E), a metal compound of the formula (XX),

where $M^G$ is Li, Na, K, Be, Mg, Ca, Sr, Ba, boron, aluminum, gallium, indium, thallium, zinc, in particular Li, Na, K, Mg, boron, aluminum or Zn, $R^{1G}$ is hydrogen, $C_1$–$C_{10}$-alkyl, $C_6$–$C_{15}$-aryl, alkylaryl or arylalkyl each having from 1 to 10 carbon atoms in the alkyl part and from 6 to 20 carbon atoms in the aryl part, $R^{2G}$ and $R^{3G}$ are each hydrogen, halogen, $C_1$–$C_{10}$-alkyl, $C_6$–$C_{15}$-aryl, alkylaryl, arylalkyl or alkoxy each having from 1 to 20 carbon atoms in the alkyl radical and from 6 to 20 carbon atoms in the aryl radical, or alkoxy with $C_1$–$C_{10}$-alkyl or $C_6$–$C_{15}$-aryl, $r^G$ is an integer from 1 to 3 and $s^G$ and $t^G$ are integers from 0 to 2, with the sum $r^G+s^G+t^G$ corresponding to the valence $M^G$, where the component E) is not identical to the component C). It is also possible to use mixtures of various metal compounds of the formula (XX).

Among the metal compounds of the formula (XX), preference is given to those in which $M^G$ is lithium, magnesium, boron or aluminum and $R^{1G}$ is $C_1$–$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyln-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from monocyclopentadienyl compound A) is from 2000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment the monocyclopentadienyl complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the cation-forming compound C) to the support B) and subsequently bringing this supported cation-forming compound into contact with the monocyclopentadienyl complex A).

The component D) can likewise be reacted in any order with the components A) and, if desired, B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the α-olefin to be polymerized and the catalyst solid comprising the components A), B) and C) as described above subsequently being added.

The monocyclopentadienyl complex A) can be brought into contact with the component(s) C) and/or D) either before or after being brought into contact with the olefins to be polymerized. Preactivation using one or more components C) prior to mixing with the olefin and further addition of the same or different components C) and/or D) after the mixture has been brought into contact with the olefin is also possible. Preactivation is generally carried out at 10–100° C., in particular 20–80° C.

It is also possible for the catalyst system firstly to be prepolymerized with α-olefins, preferably linear $C_{2-10-1}$-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:1 000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1 000 to 1000:1, preferably from 1:5 to 20:1.

The catalyst systems of the present invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to nonpolar olefinic compounds, including aryl-substituted α-olefins. Particularly preferred α-olefins are linear or branched $C_2$–$C_{12-1}$-alkenes, in particular linear $C_2$–$C_{10-1}$-alkenes such as ethene, propene, 1-butene, 1-pentene, 1-hexene, 1-heptene, 1-octene, 1-decene or branched $C_2$–$C_{10}$–1-alkenes such as 4-methyl-1-pentene, conjugated and unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene and methylnorbornene and dienes such as 5-ethylidene-2-norbornene, norbornadiene or ethylnorbornadiene.

Mixtures of two or more olefins can also be polymerized. In contrast to some known iron and cobalt complexes, the monocyclopentadienyl complexes of the present invention display a good polymerization activity even in the case of higher α-olefins, so that their suitability for copolymerization deserves particular emphasis. In particular, the monocyclopentadienyl complexes of the present invention can be used for the polymerization or copolymerization of ethene or propene. As comonomers in the polymerization of ethene, preference is given to using $C_3$–$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at from −60 to 350° C. under pressures of from 0.5 to 4000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The monocyclopentadienyl complexes of the present invention and the catalyst systems in which they are present can also be prepared by means of combinatorial synthesis or their polymerization activity can be tested with the aid of these combinatorial methods.

The process of the present invention allows polymers of olefins to be prepared. The term "polymerization" as used here in the description of the present invention encompasses both polymerization and oligomerization, i.e. oligomers and polymers having molar masses $M_w$ in the range from about 56 to 3000 000 can be produced by this process.

Owing to their good mechanical properties, the olefin polymers prepared using the catalyst system of the present invention are particularly useful for the production of films, fibers and moldings.

The catalyst systems of the present invention give a very high productivity in the polymerization of olefins, offer advantages in the work-up of the polymers after the polymerization and lead to significantly fewer problems in respect of catalyst residues in the polymer. In addition, the catalyst systems of the present invention display a very good activity even at a relatively low molar ratio of aluminoxane to transition metal compound. In addition the ethylenehomo- and copolymers obtained have a lower molecular weight than those obtained with analogous carbon bridged complexes. In these polymerisation less hydrogen is therefor needed to lower the molecular weight of the polymer. In addition the comonomer incorporation at a given comomomer concentration of these complexes was much lower than the comonomer incorporation of the carbon bridged chromium complexes. The polymers are thereful useful as blend components with a low comonomer fraction.

EXAMPLES

The density [g/cm$^3$] was determined in accordance with ISO 1183.

The methyl side chain content of the polymer per 1000 carbon atoms of the polymer chain (CH$_3$/1000) was determined by IR spectroscopy.

The determination of the molar mass distributions and the mean values $M_n$, $M_w$ and $M_w/M_n$ derived therefrom was carried out by means of high-temperature gel permeation chromatography using a method based on DIN 55672 under the following conditions: solvent 1,2,4-trichlorobenzene, flow: 1 ml/min, temperature: 140° C., calibration using PE standards.

Abbreviations in the table below:
cat catalyst
t(poly) polymerization time
polymer amount of polymer formed
$M_w$ weight average molar mass
$M_n$ number average molar mass
density polymer density
prod. productivity of the catalyst in g of polymer obtained per mmol of catalyst (chromium complex) used per hour Example 1

Synthesis of ($\eta^5$-cyclopentadienyl)bis(dimethylamide)borane chromium(III) dichloride (Cyclopentadien)bis(dimethylamide)borane and lithium (cyclopentadienyl)bis(dimethylamide)borane synthesized as described by G. E. Herberich et al., Organometallics, 1996, 15, 58 by deprotonation of (cyclopentadien)bis(dimethylamino)borane with lithium tetramethylpiperidine. A solution of 0.672 g (3.95 mmol) of lithium (cyclopentadienyl) bis(dimethylamide)borane (CpB(NMe$_2$)$_2$Li) in 20 ml of tetrahydrofurane was added to a solution of 1.48 g (3.95 mmol) of chromium trichloride tris(tetrahydrofurane) [CrCl$_3$(THF)$_3$] in 30 ml of tetrahydrofurane. The resulting solution was stirred at room temperature for 12 h. After removal of the solvent the remaining residue was dissolved in 50 ml of toluene. The solvent was removed from the filtrate, the resulting product washed with hexane and dried. 0.949 g (3.32 mmol) (84%) of ($\eta^5$-cyclopentadienyl)bis (dimethylamide)borane chromium(III) dichloride (CpB (NMe$_2$)$_2$CrCl$_2$) was thus obtained as a blue powder.

Polymerization

Polymerization was carried out at 40° C. under argon in a 1 l four-neck flask provided with contact thermometer, stirrer with Teflon blade, heating mantle and gas inlet tube. The appropriate amount of MAO (10% strength solution in toluene, Cr:Al see table 1) was added to a solution of the amount of catalyst of example 1 as indicated in table 1 in 250 ml of toluene and the mixture was heated to 40° C. on a waterbath. In the case of the copolymerisation (second polymerisation in table 1), shortly before introduction of ethylene, 3 ml of hexene were placed in the flask and a further amount of hexene (7.5 ml) was introduced via a dropping funnel over a period of 15 minutes after introduction of the ethylene. Ethylene was subsequently passed through the flask at a flow rate of about 20–40 l/h at atmospheric pressure (both for homo- and copolymerisations). After the time indicated in table 1 under a constant ethylene flow, the polymerization was stopped by addition of methanolic HCl solution (15 ml of concentrated hydrochloric acid in 50 ml of methanol). 250 ml of methanol were subsequently added and the resulting white polymer was filtered off, washed with methanol and dried at 70° C.

The polymers obtained in the ethylene home and copolymerisations with the unsupported boron bridged monocyccclopentadienyl chromium complexes showed a lower molecular weight than those obtained with carbon bridged complexes. In the polymerisation using the catalyst of the instant invention less hydrogen is therefor needed to lower the molecular weight of the polymer. In addition the comonomer incorporation at a given comomomer concentration of these complexes was much lower than the comonomer incorporation of the carbon bridged chromium complexes. The polymers obtained also have a broader molecular weight distribution (Mw/Mn) which gives the improved processing properties. The polymerisation itself started with low monomer uptake, which increased during the polymerisation. The complex is therefor less prone to deactivation during the initial phase of the polymerisation.

TABLE 1

Polymerization results

| Amount of cat. [mg] | Cr:Al | t(poly) [min] | Polymer [g] | Prod. [g/mmol Cr h] | $M_w$ [g/mol] | $M_w/M_n$ | CH$_3$/1000 C. | Density [g/cm$^3$] |
|---|---|---|---|---|---|---|---|---|
| 40.2 | 1:500 | 27 | 5.7 | 315 | 64709 | 7.41 | 5.7 | 0.965 |
| 34.6 | 1:636 | 20 | 4 | 347 | 34796 | 3.22 | 7.9 | 0.945 |

I claim:

1. A monocyclopentadienyl complex in which the cyclopentadienyl system bears at least one uncharged donor bound via a boron-containing bridge and comprising one or more atoms of group 15 and/or 16 of the Periodic Table of the Elements and is bound to a metal selected from the group consisting of titanium in the oxidation state 3, vanadium, chromium, molybdenum and tungsten.

2. A monocyclopentadienyl complex as claimed in claim 1 which comprises the following structural feature of the formula (Cp)(-Z-A)$_m$M (I), where the variables have the following meanings:

Cp is a cyclopentadienyl system,

Z is a divalent bridge between A and Cp selected from the group consisting of

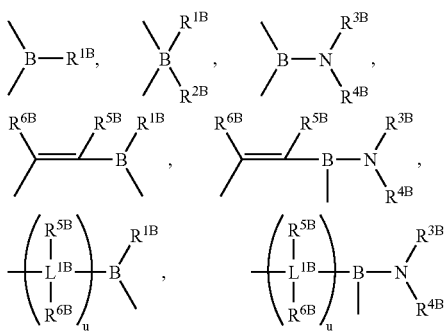

where
- $L^{1B}$ are each, independently of one another, carbon or silicon,
- $R^{1B}$–$R^{6B}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{7B}_3$, where the organic radicals $R^{1B}$–$R^{6B}$ may also be substituted by halogens and two geminal or vicinal radicals $R^{1B}$–$R^{6B}$ may also be joined to form a five- or six-membered ring and
- $R^{7B}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl radical and 6–20 carbon atoms in the aryl radical and two radicals $R^{7B}$ may also be joined to form a five- or six-membered ring,
- u is 1, 2 or 3,
- A is an uncharged donor group containing one or more atoms of group 15 and/or 16 of the Periodic Table of the Elements,
- M is a metal selected from the group consisting of titanium in the oxidation state 3, vanadium, chromium, molybdenum and tungsten and
- m is 1, 2 or 3.

3. A monocyclopentadienyl complex as claimed in claim 1 of the formula $(Cp)(-Z-A)_m MX_k$ (V), where the variables have the following meanings:
- Cp is a cyclopentadienyl system,
- Z is a divalent bridge between A and Cp selected from the group consisting of

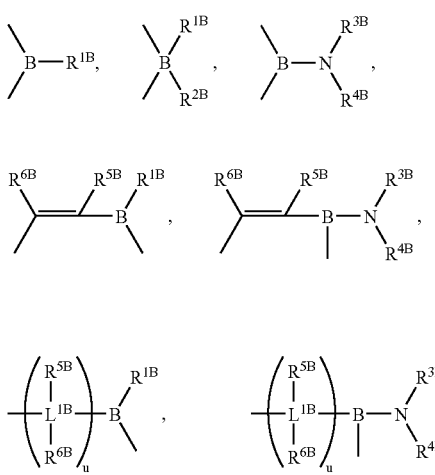

where
- $L^{1B}$ are each, independently of one another, carbon or silicon,
- $R^{1B}$–$R^{6B}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part or $SiR^{7B}_3$, where the organic radicals $R^{1B}$–$R^{6B}$ may also be substituted by halogens and two geminal or vicinal radicals $R^{1B}$–$R^{6B}$ may also be joined to form a five- or six-membered ring and
- $R^{7B}$ are each, independently of one another, hydrogen, $C_1$–$C_{20}$-alkyl, $C_2$–$C_{20}$-alkenyl, $C_6$–$C_{20}$-aryl or alkylaryl having from 1 to 10 carbon atoms in the alkyl radical and 6–20 carbon atoms in the aryl radical and two radicals $R^{7B}$ may also be joined to form a five- or six-membered ring,
- u is 1, 2 or 3,
- A is an uncharged donor group containing one or more atoms of group 15 and/or 16 of the Periodic Table of the Elements,
- M is a metal selected from the group consisting of titanium in the oxidation state 3, vanadium, chromium, molybdenum and tungsten,
- m is 1, 2 or 3,
- X are each, independently of one another, fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 cabon atoms in the alkyl part and 6–20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or a bulky noncoordinating anion,
- $R^1$–$R^2$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $SiR^3_3$, where the organic radicals $R^1$–$R^2$ may also be substituted by halogens and two radicals $R^1$–$R^2$ may also be joined to form a five- or six-membered ring,
- $R^3$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part and two radicals $R^3$ may also be joined to form a five- or six-membered ring and
- k is 1, 2, or 3.

4. A monocyclopentadienyl complex as claimed in claim 2, wherein the cyclopentadienyl system Cp has the formula (II):

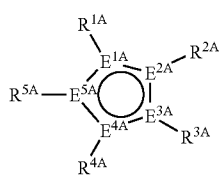

(II)

where the variables have the following meanings:
- $E^{1A}$–$E^{5A}$ are each carbon or at most one $E^{1A}$–$E^{5A}$ is phosphorus,
- $R^{1A}$–$R^{5A}$ are each, independently of one another, hydrogen, $C_1$–$C_{20}$-alkyl, $C_2$–$C_{20}$-alkenyl, $C_6$–$C_{20}$-aryl, alkylaryl having from 1 to 10 carbon atoms in the alkyl part and 6–20 carbon atoms in the aryl part, $NR^{6A}_2$, N(SiR$^{6A}_3$)$_2$, BR$^{6A}_2$, OR$^{6A}$, OSiR$^{6A}_3$, SiR$^{6A}_2$, where the organic radicals R$^{1A}$–R$^{5A}$ may also be substituted by halogens and two vicinal radicals R$^{1A}$–R$^{5A}$ may be also be joined to form a five- or six-membered ring, and/or two vicinal radicals R$^{1A}$–R$^{5A}$ are joined to form a heterocycle which contains at least one atom from the group consisting of N, P, O and S, with 1, 2 or 3 substituents, preferably 1 substituent, R$^{1A}$–R$^{5A}$ being a group -Z-A, and R$^{6A}$ are each, independently of one another, hydrogen, C$_{1-20}$-alkyl, C$_{2-20}$-alkenyl, C$_{6-20}$-aryl, alkylaryl having from 1 to 10 carbon atoms in the alkyl part and 6–20 carbon atoms in the aryl part and two geminal radicals R$^{6A}$ may also be joined to form a five- or six-membered ring.

5. A monocyclopentadienyl complex as claimed in claim 2, wherein the cyclopentadienyl system Cp together with -Z-A has the formula (IV):

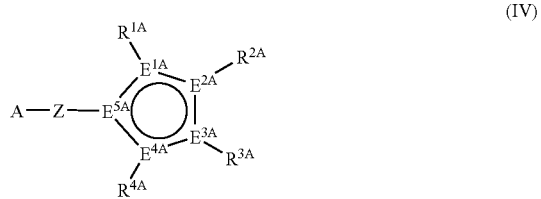

(IV)

where the variables have the following meanings:

E$^{1A}$–C$^{5A}$ are each carbon or at most one E$^{1A}$ to E$^{5A}$ is phosphorus, R$^{1A}$–R$^{4A}$ are each, independently of one another, hydrogen, C$_1$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part, NR$^{6A}_2$, N(SiR$^{6A}_3$)$_2$, OR$^{6A}$, OSiR$^{6A}_3$, SiR$^{6A}_3$, BR$^{6A}_2$, where the organic radicals R$^{1A}$–R$^{4A}$ may also be substituted by halogens and two vicinal radicals R$^{1A}$–R$^{4A}$ may be also be joined to form a five- or six-membered ring, and/or two vicinal radicals R$^{1A}$–R$^{4A}$ are joined to form a heterocycle which contains at least one atom from the group consisting of N, P, O and S, R$^{6A}$ are each, independently of one another, hydrogen, C$_{1-20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part and two geminal radicals R$^{6A}$ may also be joined to form a five- or six-membered ring, A is a donor group containing one or more atoms of group 15 and/or 16 of the Periodic Table of the Elements, Z is a divalent bridge between A and Cp selected from the group consisting of

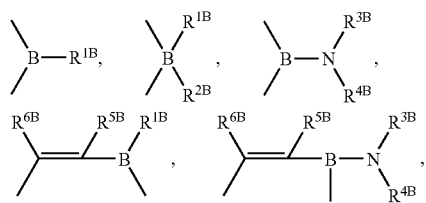

-continued

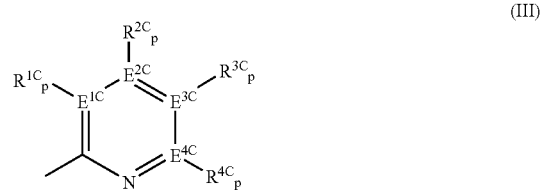

where

L$^{1B}$ are each, independently of one another, carbon or silicon,

R$^{1B}$–R$^{6B}$ are each, independently of one another, hydrogen, C$_1$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part or SiR$^{7B}_3$, where the organic radicals R$^{1B}$–R$^{6B}$ may also be substituted by halogens and two geminal or vicinal radicals R$^{1B}$–R$^{6B}$ may also be joined to form a five- or six-membered ring and R$^{7B}$ are each, independently of one another, hydrogen, C$_1$–C$_{20}$-alkyl, C$_2$–C$_{20}$-alkenyl, C$_6$–C$_{20}$-aryl or alkylaryl having from 1 to 10 carbon atoms in the alkyl radical and 6–20 carbon atoms in the aryl radical and two radicals R$^{7B}$ may also be joined to form a five- or six-membered ring and u is 1, 2 or 3.

6. A monocyclopentadienyl complex as claimed in claim 2, wherein A is an unsubstituted, substituted or fused, heteroaromatic ring system.

7. A monocyclopentadienyl complex as claimed in claim 2, wherein A has the formula (III):

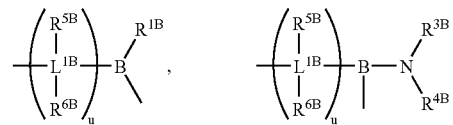

(III)

where the variables have the following meanings:

E$^{1C}$–E$^{4C}$ are each carbon or nitrogen,

R$^{1C}$–R$^{4C}$ are each, independently of one another, hydrogen, C$_1$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part or SiR$^{5C}_3$, where the organic radicals R$^{1C}$–R$^{4C}$ may also be substituted by halogens or nitrogen and further C$_1$–C$_{20}$-alkyl, C$_2$–C$_{20}$-alkenyl, C$_6$–C$_{20}$-aryl, alkylaryl having from 1 to 10 carbon atoms in the alkyl part and 6–20 carbon atoms in the aryl part or SiR$^{5C}_3$ groups and two vicinal radicals R$^{1C}$–R$^{4C}$ or R$^{1C}$ and Z may also be joined to form a five- or six-membered ring, R$^{5C}$ are each, independently of one another, hydrogen, C$_1$–C$_{20}$-alkyl, C$_2$–C$_{20}$-alkenyl, C$_6$–C$_{20}$-aryl or alkylaryl having from 1 to 10 carbon atoms in the alkyl part and 6-carbon atoms in the aryl part and two radicals R$^{5C}$ may also be joined to form a five- or six-membered ring and p is 0 when E$^{1C-4C}$ is nitrogen and 1 when E$^{1C-4C}$ is carbon.

8. A monocyclopentadienyl complex as claimed in any of claim 1, wherein Z is selected from the group consisting of BR$^{1B}$, BNR$^{3B}$R$^{4B}$, C(R$^{5B}$R$^{6B}$)—BR$^{1B}$ and C(R$^{5B}$R$^{6B}$)—BNR$^{3B}$R$^{4B}$.

9. A monocyclopentadienyl complex as claimed in claim 1, wherein M is chromium.

10. A catalyst system for olefin polymerization comprising

A) at least one monocyclopentadienyl complex as claimed in claim 1,
B) optionally, an organic or inorganic support,
C) optionally, one or more activating compounds,
D) optionally, one or more catalysts suitable for olefin polymerization and
E) optionally, one or more metal compounds containing a metal of group 1, 2 or 13 of the Periodic Table.

11. A prepolymerized catalyst system comprising a catalyst system as claimed in claim 10 and one or more linear $C_2$–$C_{10-1}$-alkenes polymerized onto it in a mass ratio of from 1:0.1 to 1:1 000 based on the catalyst system.

12. A process for preparing polyolefins by polymerization or copolymerization of olefins in the presence of a catalyst system as claimed in claim 10.

* * * * *

UNITED STATES PATENT AND TRADEMARK OFFICE
CERTIFICATE OF CORRECTION

| | | |
|---|---|---|
| PATENT NO. | : 7,202,373 B2 | Page 1 of 1 |
| APPLICATION NO. | : 10/525215 | |
| DATED | : April 10, 2007 | |
| INVENTOR(S) | : Shahram Mihan | |

It is certified that error appears in the above-identified patent and that said Letters Patent is hereby corrected as shown below:

At col. 40, line 62, delete "$E^{1A\_5A}$" and insert instead --$E^{1A}$-$E^{5A}$-- (per Preliminary Amendment, page 5, claim 4, line 5, dated 2/25/05).

At col. 41, line 1, before "$OSiR^{6A}_3$" insert --$OSiR^{6A}$-- (per Preliminary Amendment, page 6, claim 4, line 1, dated 2/25/05).

At col. 41, line 1, delete "$SIR^{6A}_2$" and insert instead --$SiR^{6A}_3$-- (per Preliminary Amendment, page 6, claim 4, line 1, dated 2/25/05).

At col. 42, line 62, delete first occurrence of "$E^{1C\_4C}$" and insert instead --$E^{1C}$-$E^{4C}$-- (per Preliminary Amendment, page 10, claim 7, line 6, dated 2/25/05).

At col. 42, line 62, delete second occurrence of "$E^{1C\_4C}$" and insert instead --$E^{1C}$-$E^{4C}$-- (per Preliminary Amendment, page 10, claim 7, line 6, dated 2/25/05).

At col. 42, line 64, delete "any of" (per Preliminary Amendment, page 10, claim 8, line 1, dated 2/25/05).

At col. 44, line 5, delete "$C_2$-$C_{10-1}$-alkenes" and insert instead --$C_2$-$C_{10}$-1-alkenes-- (per Preliminary Amendment, page 10, claim 11, line 2, dated 2/25/05).

Signed and Sealed this

First Day of September, 2009

David J. Kappos
*Director of the United States Patent and Trademark Office*